(12) United States Patent
Petersen et al.

(10) Patent No.: US 11,266,086 B2
(45) Date of Patent: *Mar. 8, 2022

(54) EFFICIENT PLANT TRANSFORMATION METHOD

(71) Applicant: Wisconsin Alumni Research Foundation, Madison, WI (US)

(72) Inventors: Michael William Petersen, Merrimac, WI (US); Brian Joseph Martinell, Mount Horeb, WI (US); Edward James Williams, Madison, WI (US); Amy Jo Miyamoto, Belleville, WI (US); Shawn Michael Kaeppler, Oregon, WI (US); Heidi F. Kaeppler, Oregon, WI (US); Robert Wayne Harnish, Middleton, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 281 days.

This patent is subject to a terminal disclaimer.

(21) Appl. No.: 16/243,965

(22) Filed: Jan. 9, 2019

(65) Prior Publication Data
US 2019/0208723 A1 Jul. 11, 2019

Related U.S. Application Data

(60) Provisional application No. 62/615,695, filed on Jan. 10, 2018.

(51) Int. Cl.
*A01H 4/00* (2006.01)
*C12N 15/82* (2006.01)

(52) U.S. Cl.
CPC ............ *A01H 4/00* (2013.01); *A01H 4/005* (2013.01); *C12N 15/8205* (2013.01); *C12N 15/8207* (2013.01)

(58) Field of Classification Search
CPC ... A01H 4/00; C12N 15/8205; C12N 15/8207
See application file for complete search history.

(56) References Cited

U.S. PATENT DOCUMENTS

| 10,407,685 | B2 * | 9/2019 | Adams, Jr | C12N 15/8205 |
| 2008/0280361 | A1 * | 11/2008 | Calabotta | C12N 15/8277 |
| | | | | 435/430 |

OTHER PUBLICATIONS

Chaudhary et al Plant Cell Reports vol. 21, pp. 955-960 (Year: 2003).*
Anwar et al Physiol. Mol. Biol. Plants vol. 14, No. 4, pp. 329-335 (Year: 2008).*
Bakshi, Souvika, et al. "Improved Agrobacterium-mediated transformation of cowpea via sonication and vacuum infiltration." Plant cell reports 30.12 (2011): 2281-2292.
Chen, Yurong, et al. "High throughput Agrobacteriumtumefaciens-mediated germline transformation of mechanically isolated meristem explants of cotton (*Gossypiumhirsutum* L)." Plant cell reports 33.1 (2014): 153-164.
Komari T, Takakura Y, Ueki J, Kato N, Ishida Y, Hiei Y (2006) Binary vectors and super-binary vectors. In: KanWang (ed.), and Methods in Molecular Biology, vol. 343: Agrobacterium Protocols, vol. 1, Second Edition. Humana Press Inc., Totowa, NJ, pp. 15-41.
McCabe, Dennis E., et al. "Stable transformation of soybean (Glycine max) by particle acceleration." Bio/technology 6.8 (1988): 923.
Obembe, Olawole O. "Exciting times for cowpea genetic transformation research." Australian Journal of Basic and Applied Sciences 3.2 (2009): 1083-1086.
Popelka, J. Carlos, et al. "Genetic transformation of cowpea (*Vigna unguiculata* L.) and stable transmission of the transgenes to progeny." Plant cell reports 25.4 (2006): 304-312.
seednet.ap.nic.in/Stl/htmlpages/seedmoisturetesting.htm Accessed Mar. 12, 2019.
Trick, Harold N.,et al., "SAAT: sonication-assisted Agrobacterium-mediated transformation." Transgenic Research 6.5 (1997): 329-336.
Ye, Xudong, et al. "Enhanced production of single copy backbone-free transgenic plants in multiple crop species using binary vectors with a pRi replication origin in Agrobacterium tumefaciens." Transgenic research 20.4 (2011): 773-786.

* cited by examiner

*Primary Examiner* — David H Kruse
(74) *Attorney, Agent, or Firm* — Quarles & Brady LLP

(57) ABSTRACT

Disclosed herein are methods for the production of value added explants from the seeds of dicotyledonous cultivars of interest. Also described are methods of transformation using the value added explants produced by the methods disclosed herein.

22 Claims, 32 Drawing Sheets
(31 of 32 Drawing Sheet(s) Filed in Color)

EFFICIENT PLANT TRANSFORMATION METHOD

CROSS-REFERENCE TO RELATED APPLICATIONS

This application claims priority to U.S. Provisional Application No. 62/615,695, filed Jan. 10, 2018, which is incorporated herein in its entirety.

BACKGROUND

Plant genetic transformation and gene editing are critically important methods for the field of agronomic research as well as advancing new traits of agronomic importance. Increased yield, nitrogen utilization, disease resistance, insect resistance, drought and heat tolerance, and nutritional improvement are just a few of the traits that are targets of these genome modifying techniques. Most methods of plant transformation and editing procedures are reliant on older "transformation competent" germplasm and are prone to tissue culture-induced mutations, creating unknown variables in the plant, complicating phenotypic selection. Additionally, current methods rely on preparation of competent germplasm tissues immediately prior to transformation due to the inability to store such tissues.

Therefore, a need exists for the development of storable germplasm tissues which are competent for a variety of transformation methods. Such a supply of storable tissues will create the potential for more rapid transformation of heterologous DNA of interest, as well as potentially increasing transformation efficiency.

SUMMARY OF THE INVENTION

In a first aspect, provided herein is a method of preparing a dried explant, the method comprising the steps of rehydrating a dry seed in a hydration medium, excising meristematic tissue from the rehydrated seed to form an explant, and drying the explant to form a dried explant. In some embodiments, the hydration medium comprises one or more priming agents. In some embodiments, the priming agent is selected from the group consisting of a small molecule, a nucleic acid, a polypeptide, a protein, an antibodies, a transcription factor, a biological macromolecule, a nanoparticle, and a liposome. In some embodiments, the seed is a dicot. In some embodiments, the seed is selected from the group consisting of cucumber, squash, pumpkin, zucchini, calabash, watermelon, alfalfa, clover, peas, beans, chickpeas, lentils, lupin bean, mesquite, carob, soybeans, peanuts, and tamarind.

In some embodiments, the method additionally comprises the step of incubating the explant in an incubation medium prior to drying. In some embodiments, the dried explant is capable of being stored for at least 10 days.

In some embodiments, the explant is incubated in incubation medium comprising one or more transformation supplements. In some embodiments, the transformation supplement is selected from the group consisting of a small molecule, a nucleic acid, a polypeptide, a protein, an antibodies, a transcription factor, a biological macromolecule, a nanoparticle, and a liposome.

In some embodiments, the method additionally comprise the step of transforming the explant or dried explant with a heterologous nucleic acid of interest. In some embodiments, the explant is transformed using *Agrobacterium* mediated transformation or particle bombardment prior to drying.

In a second aspect, provided herein is a dried explant generated by the methods described herein.

In a third aspect, provided herein is a method of preparing a value-added explant, the method comprising the steps of re-hydrating a dry seed in a hydration medium comprising at least one priming agent, and excising meristematic tissue from the rehydrated seed to form an explant. In some embodiments, the priming agent is selected from the group consisting of a small molecule, a nucleic acid, a polypeptide, a protein, an antibodies, a transcription factor, a biological macromolecule, a nanoparticle, and a liposome.

In some embodiments, the seed is a dicot. In some embodiments, the seed is selected from the group consisting of cucumber, squash, pumpkin, zucchini, calabash, watermelon, alfalfa, clover, peas, beans, chickpeas, lentils, lupin bean, mesquite, carob, soybeans, peanuts, and tamarind.

In some embodiments, the method additionally comprises drying the explant. In some embodiments, the explant is dried in the presence of a transformation supplement. In some embodiments, the transformation supplement is selected from the group consisting of a small molecule, a nucleic acid, a polypeptide, a protein, an antibodies, a transcription factor, a biological macromolecule, a nanoparticle, and a liposome.

BRIEF DESCRIPTION OF DRAWINGS

The patent or patent application file contains at least one drawing in color. Copies of this patent or patent application publication with color drawings will be provided by the Office upon request and payment of the necessary fee.

FIG. 3A shows freshly excised (left), dried down (center), and rehydrated (right) soybean explants. FIG. 3B shows seed axes ("explants") excised from Williams 82 raw seed without our quality added steps.

DETAILED DESCRIPTION OF THE INVENTION

Figure 1:
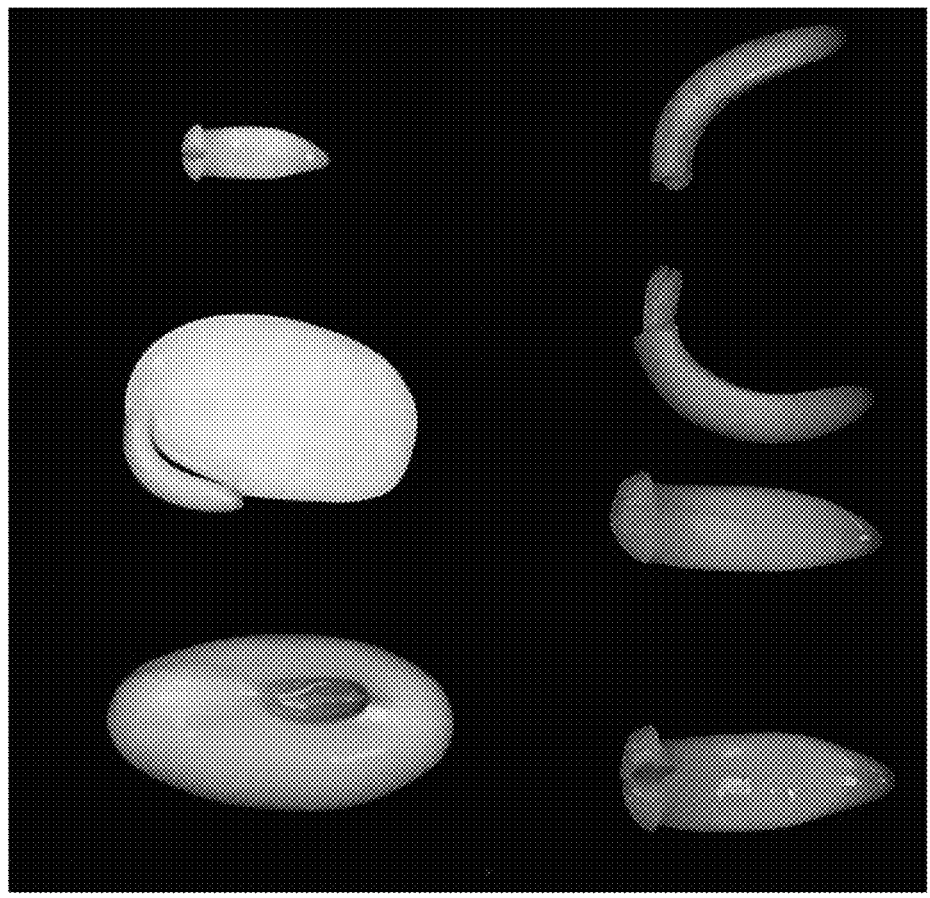
FIG. 1 shows soybean meristem explants relative to seed.

All publications, including but not limited to patents and patent applications, cited in this specification are herein incorporated by reference as though set forth in their entirety in the present application.

The present disclosure relates generally to methods for preparation and transformation of explants from legumes and other dicots. The explant preparation methods described herein allow for pretreatment of the tissues for higher explant transformation efficiency and longer explant storage following excision.

Provided herein are methods for preparing an explant suitable for transformation from a seed of a legume or other dicot. The explants generated by the methods described herein exhibit higher transformation efficiency with a broader capacity to customize the transformation process via pretreatment of the meristematic tissue used to generate the explants. Additionally, the preparation methods described herein generate an explant that is capable of being stored for longer period of time than is currently possible using existing methods. Currently, access to explants for use in transformation methods is limited to preparation of explants from meristematic tissues immediately prior to transformation. The methods described herein allow for high scale production of storable explants for more effect transformation methods. As described in further detail below, the protocols described herein allow for targeted pretreatment of the meristematic tissues used in explant preparation at various stages and with various factors to improve explant storage and transformation efficiency.

As used herein, "embryo" refers to part of a seed, consisting of precursor tissues (meristematic tissues) for the leaves, stem, and root, as well as one or more cotyledons. Once the embryo begins to grow (germinate), it becomes a seedling plant.

As used herein, "meristem" or "meristematic tissue" refers to the portion of a seed that consists of undifferentiated cells, the meristematic cells, which differentiate to produce multiple plant structures including stem, roots, leaves, germline tissues and seeds. The meristematic cells are the targets for transformation to obtain transgenic plants.

As used herein, "explant" refers to the target material for transformation.

As used herein, "germline transformation" refers to the transformation of a gene of interest into cells that give rise to pollen or ovule thus into seed.

In a first aspect, provided herein is a method for preparing an explant from the meristematic tissue of a seed, where the method generally comprises the steps of drying the seed, surface sterilizing the seed, imbibing the seed until sufficiently hydrated, excising meristematic tissue from the hydrated seed to generate an explant, and optionally drying the excised meristematic tissue to generate the storable explant for transformation. The explants generated by the methods described herein are suitable for use in any transformation method known in the art.

The methods described herein also include one or more priming steps in which one or more priming agents are added to either the hydration medium during imbibing of the seed or to the explant as it is drying to generate a value added explant (VAE). As used herein, the term "value added explant" refers to an explant prepared by the methods described herein when a priming factor has been included in the hydration medium or a transformation supplement is included during drying of the explant.

The method includes a first step of drying a seed or acquiring a dried seed from which the explant will be generated. Preferably, a dry seed for use in the methods of the present invention will have a moisture content of between 1% and 25% (e.g., 1%, 2%, 3%, 4%, 5%, 6%, 7%, 8%, 9%, 10%, 12%, 14%, 15%, 17%, 18%, 20%, 22%, or 25%). Seeds dried for storage and use in food or agriculture applications will have a storage moisture content under 15%. Ideally seeds are grown and harvested to achieve a viable embryo and are grown and harvested and cleaned to achieve blemish-free identity preserved seeds free of plant diseases and microbes that could interfere with sterile tissue culture. It may be desirable to treat the plants with fungicides and or natural or synthetic plant regulators to improve embryo viability, embryo storage quality, seed coat entactness, seed vigor, percent germination cell response in tissue culture and transformation.

Seeds from which explants are to be prepared may be harvested from any dicotyledonous cultivar of interest. In some embodiments, the seed is from a gourd. Gourds from the family cucurbitacaea may include, but are not limited to, cucumbers, squash, pumpkin, zucchini, calabash, melons and watermelon. In some embodiments the seed is a cucumber. In some embodiments, the seed is a legume. Legumes from the family fabaceae include, but are not limited to, alfalfa, clover, peas, beans, chickpeas, lentils, lupin bean, medick, birds-foot trefoil, mesquite, carob, soybeans, peanuts, and tamarind.

In some embodiments of the present invention, the dry seed is surface sterilized. Any means known in the art for surface sterilization can be used. Suitable methods for surface sterilization may include, but are not limited to, exposure of the seed surface to radiation, UV light, oxidizing gasses, heat, plasma, disinfecting solvents and agents. In some embodiments, the seed is surface sterilized with a chemical agent such as sodium hypochlorite. In some embodiments, the seed is surface sterilized with an antibacterial or antifungal agent. In some embodiments, the seed is surface sterilized with ethanol (e.g., 20%, 30%, 40%, 50%, 60%, 70%, 80%, 90%, or 100% ethanol).

The dry seed, which in some embodiments has undergone surface sterilization, is imbibed under conditions that support hydration of the seed. The dry seed is hydrated in a hydration medium and for a time sufficient for the seed reach a moisture content of between 30% and 75% (e.g., 30%, 32%, 35%, 37%, 38% 40%, 42%, 45%, 47%, 50%, 55%, 58%, 60%, 65%, and 70% and 75%). In some embodiments, the seed is hydrated for at least 12 hours. In some embodiments, the seed is hydrated between 2 and 24 hours (e.g., at least 2, 3, 4, 5, 6, 7, 8, 9, 10, 12, 14, 16, 18 or 20 hours and less than 24, 22, 20, 18, 16, 15, 14, 13, 12, 11, 10, 9, 8, 7 or 6 hours.).

The hydration medium used for hydration of the seed maybe any suitable sterile hydration medium known in the art which supports survival of the meristematic tissue in the seed. In some embodiments, the hydration medium is a modified sterile water which includes antibiotics or antifungals. In some embodiments, the hydration medium is a tissue culture medium which includes natural or synthetic plant growth regulators, plant tissue culture nutrients, a carbon source or a non-nutritive osmoregulator. In one embodiment, the hydration medium is bean germination medium which includes the components outline in Table 1 of Example 1.

In some embodiments of the invention, the hydration medium may optionally include one or more priming factors for pretreatment of the meristematic tissue. As used herein, "priming factor" references to any molecule or substance included in the hydration medium which promotes survival and storage of the prepared explant or that promotes or increases the transformation efficiency of the prepared explant. Priming factors for use in the hydration medium of the present invention may include, but are not limited to, small molecules, biological molecules such as nucleic acids, polypeptides, proteins, antibodies, transcription factors, and macromolecules or complexes thereof, nanoparticles, liposomes, and cell-penetrating peptides. In some embodiments, the priming factor is a plant growth factor including, but not limited to, thidiazuron (TDZ), 6-benzylaminopurine (BAP), polyethylene glycol (PEG), 2,4-dichlorophenoxyacetic acid (2,4-D), Paczol™, gibberellic acid (GA3), indole-3-acetic acid (IAA), indole-3-butyric acid (IBA), 1-naphthaleneacetic acid (NAA), forchlorfenuron (CPPU), spectinomycin, streptomycin, glyphosate, glufosinate, bialophos, hygromycin, amikacin, tobramycin, imazapyr, dicamba, polyvinylpryyolidone (PVP), polyvinylpolypyrrolidone (PVPP), acetosyringone, salicylic acid, proline, betaine, ethylene, brassinosteroids, nitrates, and gibberellins. In some embodiments, the priming agent is selected from the group consisting of TDZ, BAP, GA3, IAA, IBA, and NAA.

Following hydration of the seed, meristematic tissue is excised to form an explant. Excision of the meristematic tissue may be performed by any means know in the art in which the seed coat and cotyledons are removed from the seed. Suitable methods for the excision of the meristematic tissue may include, but are not limited to manual processing, wet milling using a series of rollers and spray nozzles, adjustable grinding plates rods, knives and wheels. These may be composed of, but are not limited to, ceramics, metals, and synthetic polymers. Induced pressure, injected gasses, vacuum and turbulence are also suitable methods. Excision methods may be broadly characterized as machine excision and manual or hand-excision based on the presence or absence of machines or mechanical assistance in the excision process. Hydrated explants may be stored in suitable storage medium for up to 7 days. Suitable storage medium for the hydrated explants may be any medium that supports survival and competence of the explant tissue.

Following excision, the explant may be dried. Desiccation of the explant may be performed by any means known in the art such that the moisture content of the dry explant is between 1% and 25% (1% to 25%, 1% to 20%, 1% to 15%, or 1% to 10%). Suitable methods for desiccating the explant may include, but are not limited to, drying in the presence of air with and without an added dehumidifying agent. In some embodiments, the explants are dried in a laminar flow hood. In some embodiments, the explants are dried in a dehumidifier. In some embodiments, the drying is carried out using controlled chambers such as percivals or dehydrators that control any combination of temperature, humidity, air flow, and time. In some embodiments, commercial seed dryers may be used. In some embodiments, a Bryair system is used. In some embodiments, the explants are dried at a temperature between 0° C. and 35° C. for at least 5 hours (e.g., at least 5, 7, 9, 12, 15, 18, 24, 30, 36, 42, 48, 72, 96 or 120 hours) and up to 2 weeks (e.g., up to 1, 2, 3, 4, 5, 6, 7, 8, 9, 10, 11, 12, 13, or 14 days) under conditions with a relative humidity between about 15% and about 40% (e.g., 15%, 20%, 25%, 30%, 35% or 40%). In some embodiments it may be beneficial to control rates of drying by tightly controlling temperature, humidity, air flow, and time. In some embodiments, the explant is dried at a temperate between 20° C. and 30° C. under conditions with a relative humidity between 25% and 35% for about 12 hour to 48 hours. In some embodiments, the explant is dried at a temperate of about 20° C. under conditions with a relative humidity of about 30% for about 24 hours.

Prior to drying, the explant may be incubated or pre-treated in an incubation medium to improve transformation efficiency or to improve the storage stability of the explant when dried. The incubation medium may include one or more transformation supplements. Transformation supplements for use during desiccation of the explant of the present invention may include small molecules, biological molecules such as nucleic acids, polypeptides, proteins, antibodies, transcription factors, and macromolecules or complexes thereof, nanoparticles, liposomes, *Agrobacterium*, *Rhizobium*, and cell-penetrating peptides. In some embodiments, the transformation supplement is a plant growth factor, cell protectant agent including, or other agent including, but not limited to, thidiazuron (TDZ), acetosyringone, 6-benzylaminopurine (BAP), polyethylene glycol (PEG), alginates and alginate complexes, starches, celluloses, synthetic polymers, gums, waxes, proline, betaine, polyvinylpryyolidone (PVP), polyvinylpolypyrrolidone (PVPP), salicylic acid, calcium sources, silicone sources, colchicine, 2,4-dichlorophenoxyacetic acid (2,4-D), Paczol™, gibberellic acid (GA3), gibberellin (GA) pathway inhibitors, indole-3-acetic acid (IAA), indole-3-butyric acid (IBA), 1-naphthalaneacetic acid (NAA), forchlorfenuron (CPPU), spectinomycin, streptomycin, glyphosate, glufosinate, bialophos, hygromycin, amikacin, tobramycin, imazapyr, lyophilized *agrobacterium*, lyophilized rhizobium, and potassium hydroxide (KOH). In some embodiments, the transformation supplement is an agent which promotes multiplication of the meristematic tissue, such as, but not limited to, TDZ, BAP, zeatin, kinetin, and CPPU. In some embodiments, the pre-treatment or incubation step may include inoculating the explant by *Agrobacterium* mediated inoculation or particle bombardment with a heterologous gene or nucleic acid of interest. In some embodiments, the pre-treatment or incubation step includes inoculating the explant by *Agrobacterium* mediated inoculation or particle bombardment with a heterologous gene or nucleic acid of interest in the presence of TDZ.

During desiccation of the explant, one or more transformation supplements may be added. As used herein, "transformation supplement" references to any molecule or substance added to the explant prior to or during desiccation which promotes survival and storage of the prepared explant or that promotes or increases the transformation efficiency of the prepared explant. Transformation supplements for use during desiccation of the explant of the present invention may include small molecules, biological molecules such as nucleic acids, polypeptides, proteins, antibodies, transcription factors, and macromolecules or complexes thereof, nanoparticles, liposomes, *Agrobacterium, Rhizobium*, and cell-penetrating peptides. In some embodiments, the transformation supplement is a plant growth factor, cell protectant agent including, or other agent including, but not limited to, thidiazuron (TDZ), 6-benzylaminopurine (BAP), polyethylene glycol (PEG), alginates and alginate complexes, starches, celluloses, synthetic polymers, gums, waxes, proline, betaine, polyvinylpryyolidone (PVP), polyvinylpolypyrrolidone (PVPP), salicylic acid, calcium sources, silicone sources, colchicine, 2,4-dichlorophenoxyacetic acid (2,4-D), Paczol™, gibberellic acid (GA3), gibberellin (GA) pathway inhibitors, indole-3-acetic acid (IAA), indole-3-butyric acid (IBA), 1-naphthalaneacetic acid (NAA), forchlorfenuron (CPPU), spectinomycin, streptomycin, glyphosate, glufosinate, bialophos, hygromycin, amikacin, tobramycin, imazapyr, lyophilized *agrobacterium*, lyophilized *rhizobium*, and potassium hydroxide (KOH). In some embodiments, the transformation supplement is an agent which promotes multiplication of the meristematic tissue, such as, but not limited to, TDZ, BAP, zeatin, kinetin, and CPPU. In some embodiments, explants are mechanically wounded prior to drying and storage. This can be achieved with exposure to ultrasound energy (e.g., sonication), liquid nitrogen, centrifugation, pressure, and chemical (ex. KOH, PEG, acids, bases), enzymes, abrasives, water jets, lasers, needles, or blades.

The dried explants are suitable for storage in a variety of conditions. Dried explants may be stored at temperatures ranging from about −200° C. to 50° C. (i.e., about −190° C. to 40° C., about −170° C. to 30° C., about −150° C. to 20° C., about −130° C. to 10° C., and about −102° C. to 0° C.) for a period of time of at least 7 days (i.e., at least 10 days, at least 30 days, at least 50 days, at least 60 days, at least 75 days, at least 90 days, and at least 120 days). Storable dried explants can also be banked to create libraries of germplasms from a variety of cultivars of agronomic significance. In some embodiments, dried explants may be stored for as little as 1 day, 2 days, 3 days or 4 days. Dried explants provide the advantage of not requiring transformation on the same day the embryo is isolated.

Dried explants may be imbibed prior to transformation with hydration medium. In some embodiments, the hydration medium includes 20% PEG4000 with 60 mg/L Captan fungicide and 30 mg/L Bravo (Daconil) fungicide. In some embodiments, the hydration medium includes 60 ppm Cleary's fungicide. In some embodiments, the concentration of PEG or sugar is varied to reduce the osmotic stress on the explants. In some embodiments, a priming factor or transformation supplement may be added to the hydration medium.

Explants generated by the methods described herein can be transformed with a heterologous gene or nucleic acid of interest by any means known in the art. Various methods have been developed for transferring genes or nucleic acids into plant tissue including particle bombardment, high velocity microprojection, microinjection, electroporation, direct DNA uptake, and bacterially-mediated transformation. Bacteria known to mediate plant cell transformation include a number of species of the Rhizobiaceae, including, but not limited to, *Agrobacterium* spp., *Sinorhizobium* spp., *Mesorhizobium* spp., *Rhizobium* spp., and *Bradyrhizobium* spp. In some embodiments, the explant is transformed used *Agrobacterium* spp. In some embodiments, the explant is transformed using particle bombardment using gold microcarriers. Suitable methods of plant transformation are described in the art, such as, for example, by McCabe et al. (McCabe, D. E., Swain, W. F., Martinell, B. J., Christou, P. (1988) *Nature Biotechnology* 6(8), 923-926), Chen et al. (Chen, Y., Rivlin, A. Lange, A., Ye, X., Vaghchhipawala, Z., Eisinger, E., Dersch, E., Paris, M., Martinell, B., Wan, Y. (2014) *Plant Cell Reports* 33(1), 153-164), Ye et al. (Ye, X., Williams, E. J., Shen, J., Johnson, S., Lowe, B., Radke, S., Strickland, S. Esser, J. A., Petersen, M. W., and Gilbertson, L. A. (2011) *Transgenic Research* 20(4), 773-7860), and *Plant Transformation Technologies* (Edited by C. Neal Stewart, Alisher Touraev, Vitaly Citovsky and Tzvi Tzfira© 2011 Blackwell Publishing Ltd. ISBN: 978-0-813-82195-5.)

The heterologous gene or nucleic acid of interest may be any gene or nucleic acid which may confer a particular desirable trait or phenotype in the transformed plant. Examples of suitable genes of agronomic interest envisioned by the present invention would include but are not limited to genes for disease, insect, or pest tolerance, herbicide tolerance, genes for quality improvements such as yield, nutritional enhancements, environmental or stress tolerances, or any desirable changes in plant physiology, growth, development, morphology or plant product(s) including starch production, modified oils production, high oil production, modified fatty acid content, high protein production, fruit ripening, enhanced animal and human nutrition, and biopolymers production. Also environmental stress resistance, pharmaceutical peptides and secretable peptides, improved processing traits, improved digestibility, low raffinose, industrial enzyme production, improved flavor, nitrogen fixation, hybrid seed production, fiber production and biofuel production. Any of these or other genetic elements, methods, and transgenes may be used with the invention as will be appreciated by those of skill in the art in view of the instant disclosure. The heterologous gene or nucleic acid of interest may also be a sequence which can affect a phenotype of interest by encoding an RNA molecule that cases the targeted inhibition of expression on an endogenous gene via gene silencing technologies.

The heterologous gene or nucleic acid of interest may be transformed in the form of a vector. Any suitable vector design known in the art may be used with the explants of the present invention. In some embodiments, the vector will additionally include one or more selectable or screenable markers. The selectable or screenable marker may confer upon the plant tissue resistance to an otherwise toxic compound. A number of screenable or selectable marker are known in the art and can be used in the present invention. The screenable marker may be fluorescent (e.g., RFP) or non-fluorescent (e.g., GUS). More than 20 selectable marker genes have been reported in the transformation of higher plants (Komari T, Takakura Y, Ueki J, Kato N, Ishida Y, Hiei Y (2006) Binary vectors and super-binary vectors. In: Kan-Wang (ed.), and *Methods in Molecular Biology*, vol. 343: *Agrobacterium Protocols*, Vol. 1, Second Edition. Humana Press Inc., Totowa, N.J., pp. 15-41).

Following inoculation, the explant may be incubated or co-cultured. Explants may be co-cultured in medium suitable for the survival of the explant. Co-culture medium may be supplemented with one or more factors to promote multiplication of meristematic cells, suppress apical dominance, or both. Explants may be co-culture in medium including thidiazuron (TDZ). In some embodiments, the co-culture medium includes nystatin, tiabendazole (TBZ), and lipoic acid. In some embodiments, the co-culture medium includes Gamborg's B-5 salt mix, glucose, nystatin, tiabendazole (TBZ), and lipoic acid. In some embodiments, the co-culture medium includes acetosyringone. The explant co-culture may be freely suspended or surrounded by the co-culture medium. The explant co-culture maybe also include solidified co-culture medium, such as medium solidified with agarose, and the explants may be cultured on top of or within the solidified co-culture medium. Any suitable volume of co-culture medium may be used. In some embodiments, the explant co-cultures are agitated. For example, the explant co-cultures may be agitated on an orbital shaker at a speed between about 110 RPM and about 160 RPM depending on the size of the co-culture vessel and volume of co-culture medium. In some embodiments, the inoculated explants are co-cultured in medium including excess inoculum. Following inoculation and co-culture explants are grown on appropriate selection medium to select for positively transformed explants.

In some embodiments, the explant is transformed using particle bombardment using gold microcarriers. Follow precipitation of the heterologous gene or nucleic acid of interest onto the gold microcarriers, cowpea or dry bean explants are subjected to particle bombardment using the gold microcarriers. Follow particle bombardment, explants are grown on appropriate selection medium to select for positively transformed explants.

The present invention has been described in terms of one or more preferred embodiments, and it should be appreciated that many equivalents, alternatives, variations, and modifications, aside from those expressly stated, are possible and within the scope of the invention.

Example 1

The embodiment described here demonstrates a method for generating a soybean VAE and improved transformation of the soybean VAE.

Materials and Methods

Figure 2:
FIG. 2 shows a Soybean Williams82 value added explant (VAE) dried for 72 hours in Bryair at 30 C and stored at −20 C (left); and transient GUS activity in Soybean Williams 82 VAE dried for 72 hours in laminar flow hood (LFH) after co-culture with *Agrobacterium* (right).
Figure 2:
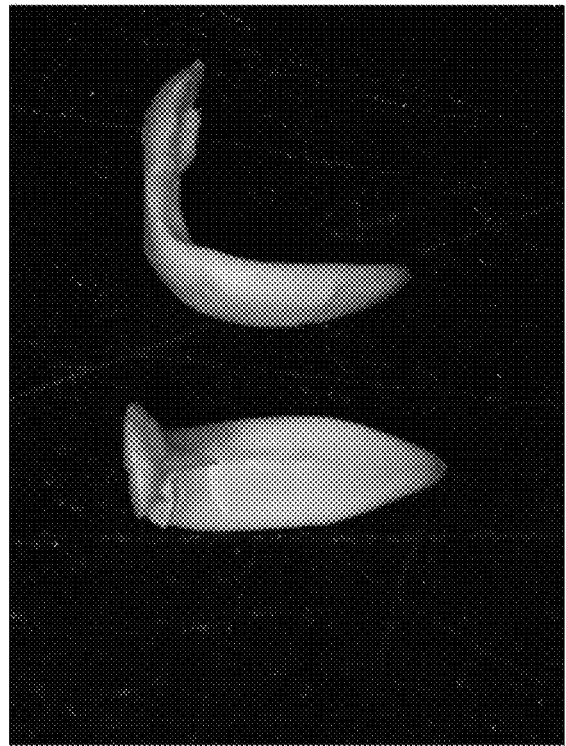
Figure 3A:
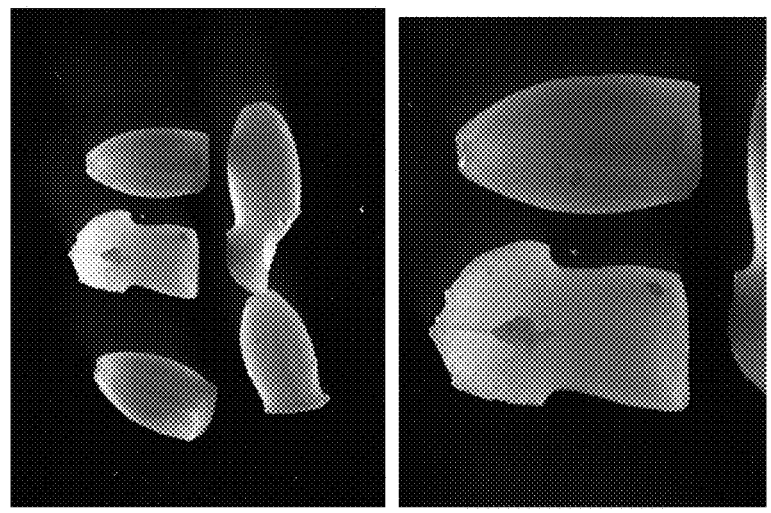
FIGS. 3A-3B show a comparison of excised meristem tissues.
Figure 3B:
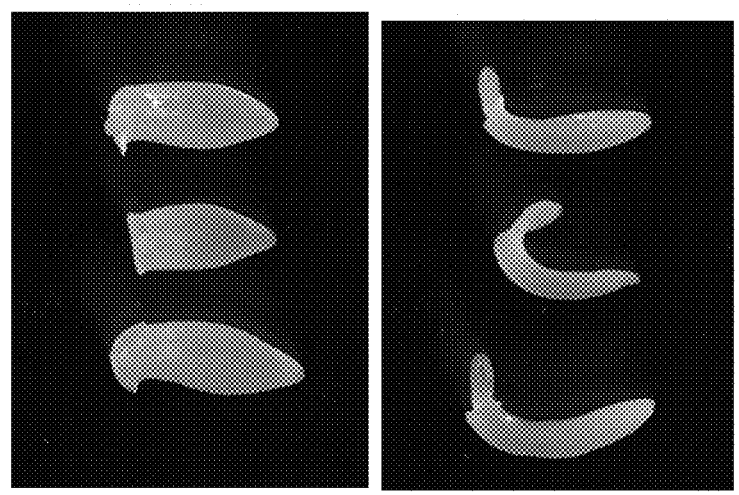

Soybean seeds were surface sanitized in 20% Clorox (from concentrated Clorox with 8.25% sodium hypochlorite) for 5 minutes, rinsed 5× with sterile RO water, and then primed by allowing them to sit for 2 hrs at room temperature. Seeds were then imbibed in WCIC Bean Germination Media (BGM) overnight. Meristem explants were prepared the next day by removing seed coats and cotyledons from the seed using either a manual process or in a wet mill consisting of a series of rollers and spray nozzles. Meristem explants were then either dried under a variety of conditions, or used fresh. Drying of explants was performed in either a Laminar Flow Hood (LFH) with explants resting on a filter paper exposed to air, or in a BryAir seed dryer (model VFB-3-E-DXA) on filter paper. For internal moisture determination, 0.5-1 g of dried material was placed in a 103 C oven for 16-18 hours, contents allowed to cool, then re-weighed. For use in transformation, dried explants—designated as soy VAEs (value added explants) were incubated 1-2 hours at room temperature in 20% PEG4000 (dissolved in sterile distilled water) supplemented with 60 mg/L Captan fungicide and 30 mg/L Bravo (Daconil) fungicide. Explants were then rinsed 5-6× with sterile distilled water and inoculated with *Agrobacterium*. FIG. 1 shows excised soybean meristem explants relative to an imbibed seed, and FIG. 2 shows dried soy VAEs as well as transient activity in meristem of soy VAE after co-culture with *Agrobacterium*. FIG. 3A shows freshly excised soy, dried soy VAE, and rehydrated soy VAE. FIGS. 3A and 3B show VAEs (3A) as compared to explants directly from just dry seed (3B).

TABLE 1

WCIC BGM (Wisconsin Crop Innovation Center's Bean Germination Medium): WPM salt mix (Phytotechnology Laboratories L449: McCown's Woody Plant Medium, with macro and micronutrients and vitamins; no sucrose). Can be autoclaved and stored for 8 weeks prior to addition of post autoclave chemicals.

| Ingredients and Notes | Amount to add per liter (milligrams) |
| --- | --- |
| Phytotechnology Laboratories L449 | 2,410 |
| Sucrose | 20,000 |
| pH to 5.8 with 1N KOH and autoclave | |
| Add the following fresh before use: | |
| Captan powder (50WP) | 60.0 |
| Daconil powder (82DP) | 30.0 |
| Cefotaxime | 125.0 |

Figure 4A:
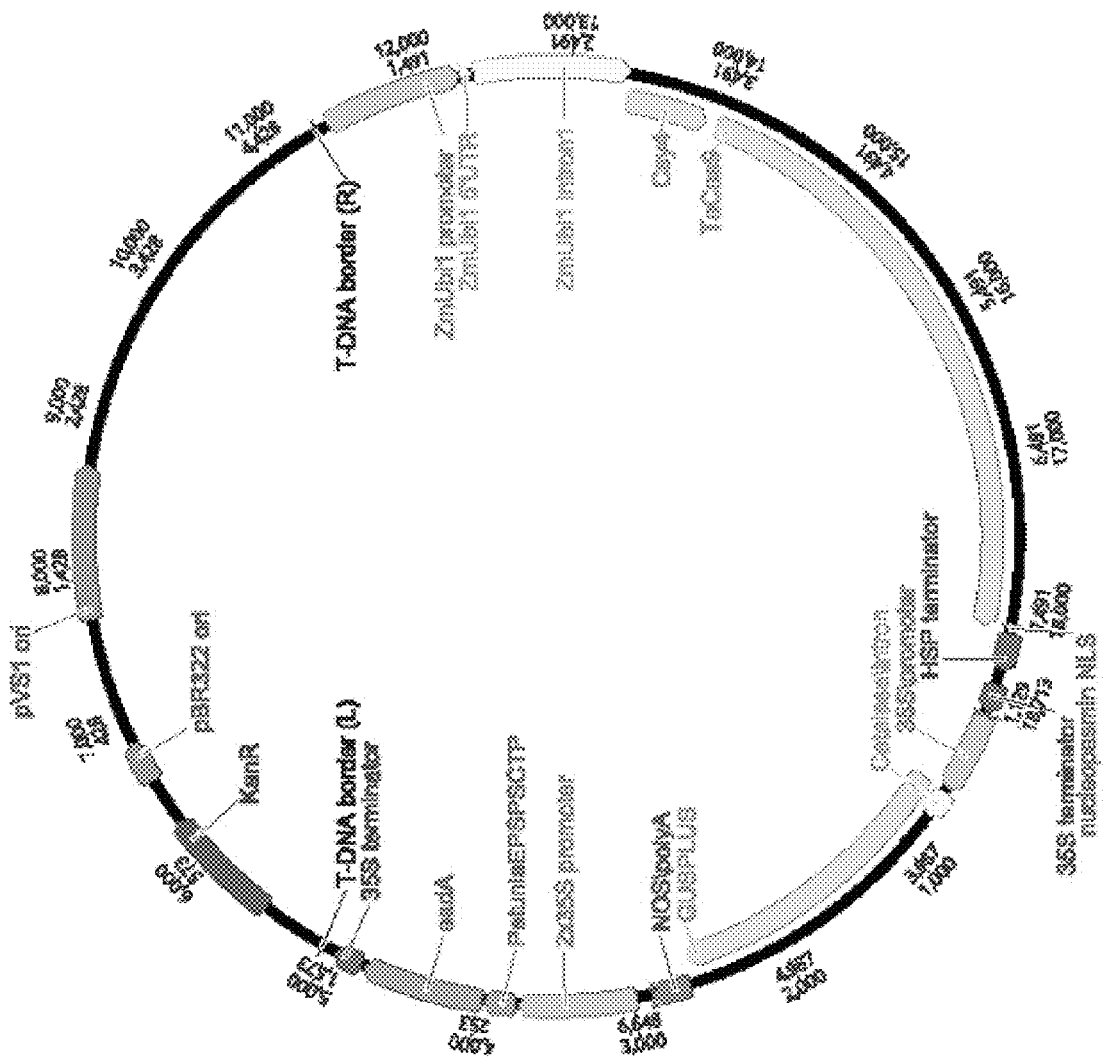
FIG. 4A shows a vector map of VS225.
Figure 4B:
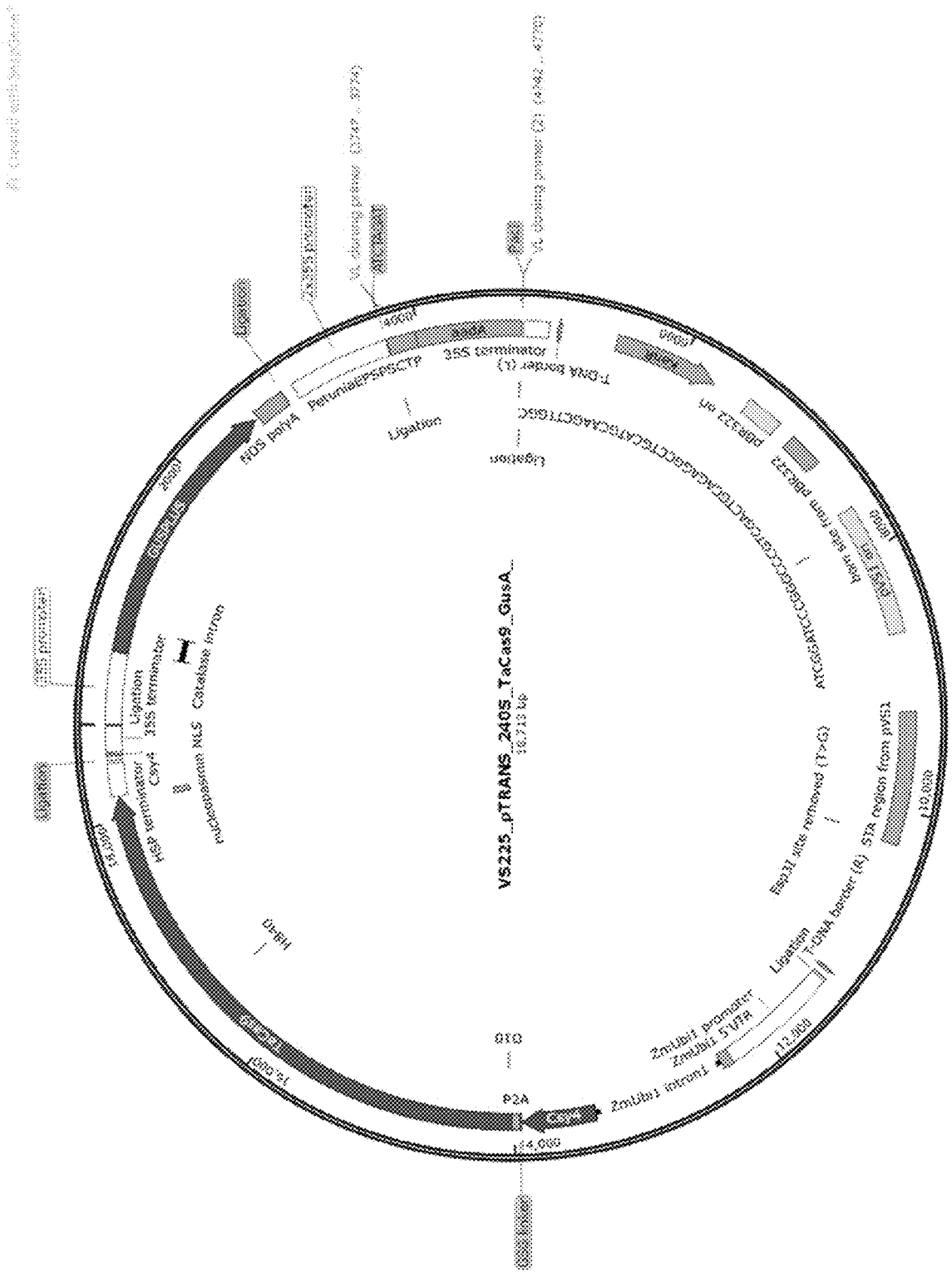
FIG. 4B shows a vector map of VS225 in Snapgene format.
Figure 4C:
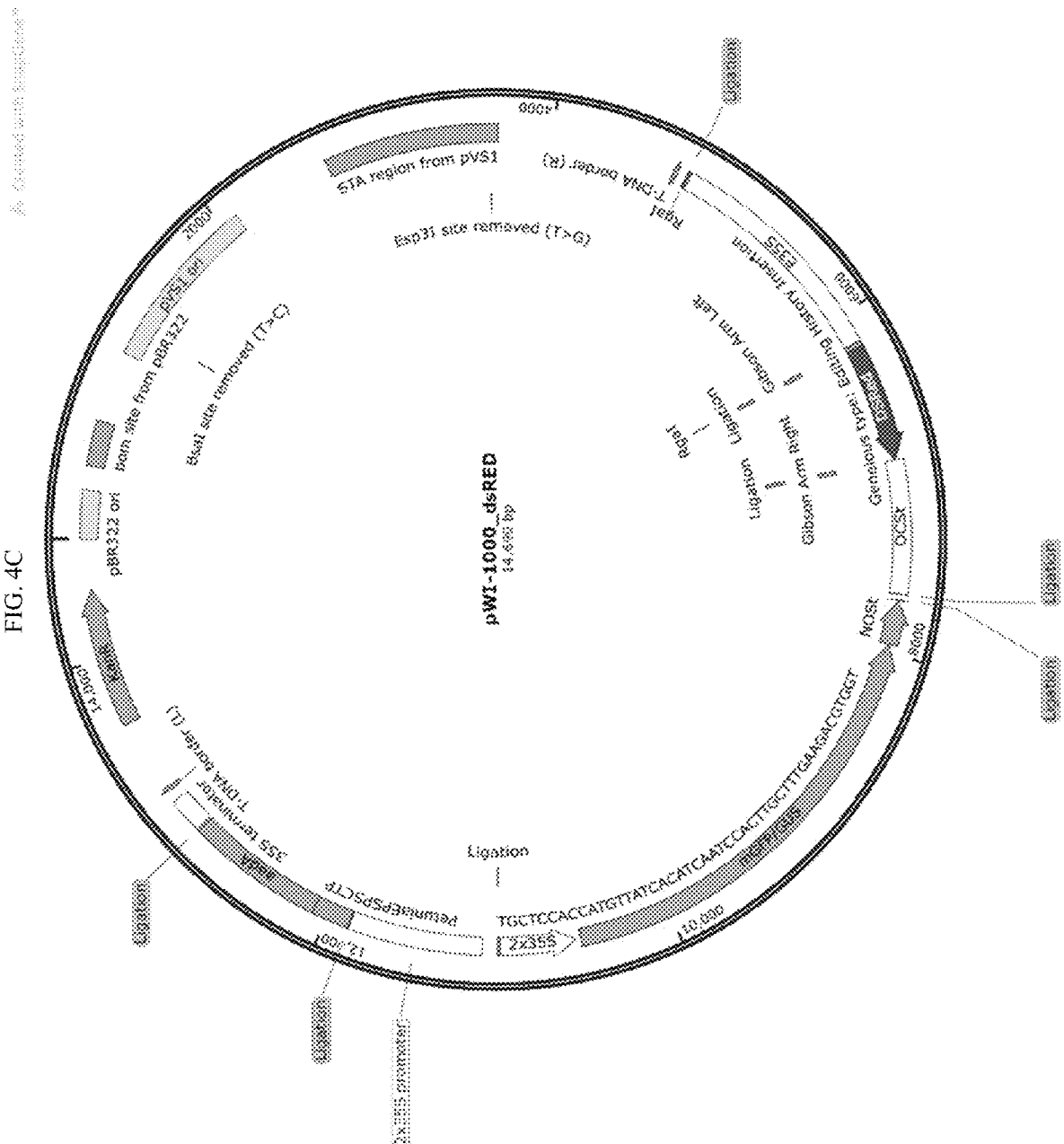
FIG. 4C shows a vector map of pWI-1000_dsRED.

*Agrobacterium* inoculum was prepared under laminar flow hood from overnight cultures derived from 20% glycerol stocks stored at −80 C. Glycerol stocks were allowed to thaw, and approximately 50 ul stock was added to 50 ml LB with 50 mg/L kanamycin (GV3101 strain); or 250 ul stock to 50 ml LB with 50 ppm kanamycin and 100 ppm carbenicillin (AGL1 strain). The VS225 binary construct with pVS1 origin of replication conferred resistance to kanamycin, and had aadA, gus, and cas9 genes on its T-DNA. The pWI-1000 binary construct with pVS1 origin of replication conferred resistance to kanamycin, and had aadA and gus on its T-DNA. The pWI-1000 dsRED binary construct with pVS1 origin of replication conferred resistance to kanamycin, and had aadA, gus, and rfp (dsRED) on its T-DNA. Cultures were grown overnight at 28° C. 200 RPM on orbital shaker (Innova 4400 incubator shaker). The next morning optical densities of cultures at 660 nm (OD660) were checked (Hach DR5000™ Spectrophotometer) under laminar flow and then centrifuged at 2619×g for 20 min (H6000A rotor on Sorvall® RC3B centrifuge). Pelleted bacteria was re-suspended in WCIC INO media under laminar flow, diluted to OD660 0.3-0.45, and incubated at room temperature 150 RPM until used (VWR orbital shaker). In some experiments acetosyringone was added to inoculum at 100 uM to help induce the vir operon. Sample constructs are shown in FIGS. 4A-4C.

Figure 5A:
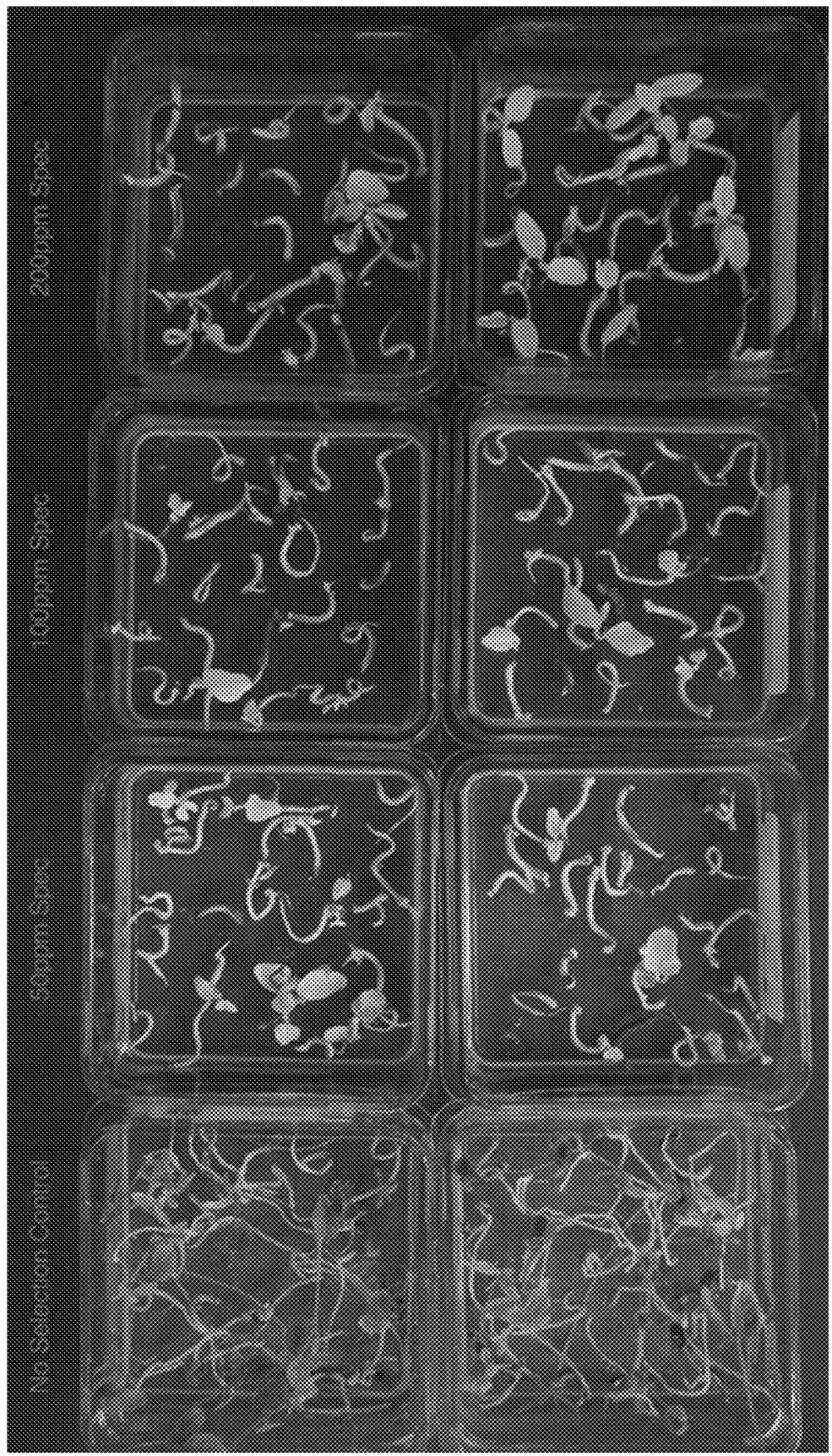
FIG. 5A shows spectinomycin selection titration at 5 weeks using W82 Soybean VAEs.
Figure 5B:
FIG. 5B shows soybean value added explants (VAE) in spectinomycin titrations.

We ran a titration of spectinomycin selection levels on non-inoculated soybean VAEs, and could see visible bleaching and suppression of shooting and rooting as low as 50 ppm at 5 weeks (FIG. 5).

Meristem explants were inoculated under laminar flow in inverted PlantCon® (approximately 25 ml inoculum per PlantCon®) (MP Biomedicals, LLC Cat. 26-722-06) and sonicated for 20 s, 45+/−2 kHz (L&R Sonicator Quantrex 450) in a 0.1% Triton X-100 water bath (Triton X-100 from Sigma #9002-93-1). Inoculated explants were incubated with inoculum for additional 30 min at room temperature at 75 RPM. Excess inoculum was then removed, and explants co-cultured in PlantCons® with 2.5 ml WCIC INO media supplemented with 50 mg/L nystatin, 10 mg/L TBZ, and 95 uM lipoic acid at 23 C 16/8 photoperiod. In some experiments this co-culture media was further supplemented with 1 mg/L TDZ in attempt to multiply meristematic cells and possibly suppress apical dominance. In some experiments acetosyringone was added to inoculum and/or co-culture medium at 100 uM as an inducing agent for the virulence cascade in the the vir operon.

TABLE 2

WCIC INO and Co-culture Medium: Gamborg's B-5 salt mix (Phytotechnology Laboratories G398: Gamborg's B-5 Plant Medium, with macro and micronutrients and vitamins; no sucrose). Can be autoclaved and stored for 8 weeks prior to addition of post autoclave chemicals.

| Ingredients and Notes | Amount to add per liter (milligrams) |
|---|---|
| Phytotechnology Laboratories G398 | 1,284 |
| Glucose | 30,000 |
| MES | 2,800 |
| pH to 5.4 with 1N KOH and autoclave | |
| Add the following fresh before use: | |
| Nystatin/Thiabendazole (DMSO) Stock Nystatin 50 mg + Thia 10 mg in 1,000 uL DMSO) | Use 1.0 mL per L (Nystatin-50 mg/L + Thiabendazole −10 mg/L) to co-culture media |
| Lipoic Acid (50 mg per ml stock in 100% Ethanol) | Use at 500 uL per Liter (95 uM) to co-culture media |

After co-culture (3-5 days) explants were transferred to 200 ppm spectinomycin WCIC B5 media. When using the GV3101 strain we supplemented this selection media with 200-400 mg/L carbenicillin to knock Agrobacterium overgrowth down. Explants were transferred to fresh selection media as needed based on overgrowth (generally every 3-4 weeks for AGL1 and every 5-6 weeks for GV3101).

Shoots from spectinomycin resistant plantlets were harvested and rooted on 200 ppm spectinomycin WCIC Bean Rooting Media (BRM). Rooted plants were sent to greenhouse (GH) for T1 seed set.

TABLE 3

WCIC Spectinomycin Selection Medium (WCIC B5): Gamborg's B-5 salt mix (Phytotechnology Laboratories G398: Gamborg's B-5 Plant Medium, with macro and micronutrients and vitamins; no sucrose). Can be autoclaved and stored for 4 weeks prior to addition of post autoclave.

| Ingredients and Notes | Amount to add per liter (milligrams) |
|---|---|
| Phytotechnology Laboratories G398 | 2,410.0 |
| Sucrose | 20,000 |
| Cleary's 3336 (50WP) | 60.0 |
| Ca Gluconate | 1,290.0 |
| Phytagel | 3,500.0 |
| pH to 5.8 with 1N KOH and autoclave | |
| Add the following fresh before use: | |
| Spectinomycin (100 mg/ml stock) | Use 2.0 mL per liter (200 mg/L) |
| Timetin (150 mg/ml stock) | Use 1.0 mL per L (150 mg/L) |
| Cefotaximine (100 mg/ml stock) | Use at 1,250 uL per Liter (125 mg/L) |

TABLE 4

WCIC Spectinomycin Bean Rooting Medium:

| Ingredients and Notes | Amount to add per liter (milligrams) |
|---|---|
| MS Salts (1/2X) | 2150 |
| myo-inositol | 100 |
| sucrose | 30,000 |
| pH 5.8 with KOH | |
| Agar | 8,000 |
| Autoclave 25 min | |
| Add fresh before use | |
| Spectinomycin (100 mg/ml) | Use 2.0 mL per Liter (200 mg/L) |
| Cysteine (100 mg/ml) | Use at 1.0 ml per Liter (100 mg/L) |
| Cefotaxime (100 mg/ml) | Use at 2.0 ml per Liter (200 mg/L) |
| IAA (1 mg/ml) | Use at 0.1 ml per Liter (0.1 mg/L) |
| MS Vitamins (1000X) | Use at 1.0 ml per Liter |

For particle bombardment experiments, gold-DNA "bead prep" was prepared by first washing 50 mg 0.6 um gold microcarriers (BioRad part #1652262) in 1 ml 100% ethanol and sonicating for 1 min 45 kHz. Gold was pelleted by centrifugation at 5000 rpm in microfuge (~2300×g) and ethanol removed. Gold was then re-suspended in 1 ml 100% ethanol and stored at −20 C until use. To precipitate DNA onto beads, the 50 mg gold/1 ml ethanol stock was sonicated for 1 min 45 kHz. 42 ul of this stock was transferred to an Eppendorf tube, then pelleted by centrifugation at 2500 rpm for 10 seconds, after which ethanol was removed. 500 uL sterile water was added and mixture sonicated 1 min 45 kHz. Gold was again pelleted by centrifugation at 2500 rpm for 10 seconds and water removed. 25 ul sterile water was then added, followed by sonication for 1 min 45 kHz. 2.6, 1.3, or 0.65 ug VS225 DNA was added, then sterile water to bring volume up to 245 ul. 250 ul cold 2.5 M $CaCl_2$ was added, followed by 50 ul 0.1 M spermidine. Solution was mixed by low speed vortexing. Tube was incubated on ice for approximately 1 hour with gentle inversions every 5-10 minutes. DNA/gold was pelleted at 1000 rpm (~100×g) for 2 min and supernatant removed. Pellet was then washed with 1 ml 100% EtOH w/pipette tip, then pelleted again at 1000 rpm (~100×g) for 2 min and supernatant removed 36 ul 100% EtOH was added to tube and gold completely re-suspended with low-speed vortexing. Bead prep was stored at −20 C until used, with 5 ul used per bombardment. This corresponds to 360, 180, or 90 ng DNA per blast; 290 ug gold per blast (1.2, 0.6, or 0.3 ng DNA per ug gold).

For blasting Soybean VAEs, meristem explants were incubated in 20% PEG4000 with 60 mg/L Captan and 30 mg/L Bravo for 1 hour, rinsed thoroughly, and pre-cultured overnight on WCIC EJW1 media at 28 C 16/8 photoperiod.

TABLE 5

WCIC Soybean Pre-culture Medium EJW1

| Ingredients and Notes | Amount to add per liter (milligrams) |
| --- | --- |
| MS salts no vitamins | 4300 |
| Sucrose | 30000 |
| 2,4-D | 0.2 |
| MES | 2000 |
| Cleary's 3336 | 30 |
| pH | 5.6 |
| Agarose | 4000 |
| Autoclave | |
| Carbenicillin | 250 |
| TDZ | 1 |

After preculture, Soybean VAEs were targeted on a 12% xantham gum holding media, 20 per plate, with meristems oriented upward. Prior to particle bombardment on the PDS-1000 helium gun, stop screens (BioRad part 1652336), 1350 psi rupture disks (BioRad 1652330), and macrocarrier holders (BioRad part 1652322) were sanitized for 1 min in 70% EtOH. Carrier sheets (BioRad part 1652335) were sanitized for 1 min in isopropanol. 1350 psi rupture disk was placed into the rupture disk retaining cap and screwed into the gas acceleration chamber. Stop screen was placed in the brass adjustable nest. 5 uL bead prep was deposited on the center of each carrier sheet loaded onto the macrocarrier holder and allowed to air dry. Macrocarrier holder was then turned over to place above retaining screen on brass nest. Macrocarrier cover lid was screwed on and completed macrocarrier launch assembly was placed on shelf directly under rupture disk. Gap distance between rupture disk and launch assembly was approximately 1 cm. Lid from target plate was removed and plate was placed on shelf 2 ($2^{nd}$ shelf from macrocarrier launch assembly) which is approximately 6 cm from assembly. Helium tank, PDS-1000, and vacuum were all turned on. Door was closed and vacuum applied to ~27-28 In Hg. Fire button was depressed and held down until blast was complete. Vacuum was then released and target plate removed.

After blasting, soybean VAEs were detargeted onto WCIC EJW1 media and allowed to rest overnight at 28 C 16/8 photoperiod. Explants were then placed on WCIC Spectinomycin Selection Medium and placed in 28 C 16/8 photoperiod.

T1 plants were sprayed with 1000 ppm spectinomycin (made fresh) to examine segregation of selectable marker gene. 1,658 mg Spectinomycin dihydrochloride penta-hydrate (Sigma 59007-25G, Lot number 122K0561) at a potency of 603 ug per mg was added to one liter sterile RO/DI water with 0.1% Tween 80. Plants were sprayed using a lab hand spray bottle. Application will be "over the top" only (upper surface of seedlings). Seedlings had fully expanded primary leaves and the first trifoliate leaves are just beginning to expand. Some cultivar variability was observed.

Results

Figure 6:
FIG. 6 shows the appearance of LFH dried soybean VAEs (left) vs freshly excised soybean explants (right) post co-culture.

Our transformation tests using soybean VAEs used the Agrobacterium AGL1 strain harboring VS225. Table 6 shows results from hand excised soybean VAEs dried in laminar flow hood (LFH) for 72 hours. LFH dried soybean VAEs and freshly excised soybean explants post-co-culture are shown in FIG. 6.

TABLE 6

Transformation metrics for hand excised Williams82 batch dried in LFH

| Treatment | # Explants | # T0 Plants | TF |
| --- | --- | --- | --- |
| Freshly excised, 3 day co-culture | 100 | 4 | 4% |
| Freshly excised, 5 day co-culture | 100 | 0 | 0% |
| Dried down, rehydrated, 3 day co-culture | 100 | 10 | 10% |
| Dried down, rehydrated, 5 day co-culture | 100 | 13 | 13% |

Table 7 shows transformation metrics for freshly excised Williams82 machine excised soy against and this same batch dried in Bryair at 30 C for 72 hours to generate VAE batch S8.

TABLE 7

Transformation metrics for excised Williams82 batch dried in Bryair seed dryer.

| Treatment | # Explants | # T0 Plants | TF |
| --- | --- | --- | --- |
| Fresh sample of explants dried to generate S8 | 111 | 4 | 3.6% |
| S8 - dried 72 h in 30 C. Bryair to 3% internal moisture | 271 | 0 | 0% |

Based on this and on results from the earlier hand excised material we determined drying conditions were a critical component to the success of this protocol. We suspected the Bryair seed drier was possibly drying the explants too rapidly, causing damage to the tissue. Using AGL1/VS225 we inoculated a series of soybean VAEs which had been machine excised the same day, but dried under alternate conditions (soybean VAE batches S17a-f). Transformation metrics for this study are given in Table 8, which demonstrated proof of concept of Bryair use for generating usable soybean VAEs as well as giving a broad range of percent moistures available for us to use.

TABLE 8

Transformation metrics for Williams82 Soy VAE Batches S17a-f (AGL1/VS225)

| Treatment | Internal Moisture | # Explants | # T0 Plants | TF |
| --- | --- | --- | --- | --- |
| S17a; 5 h dry in 20 C. Bryair | 12.4% | 47 | 0 | 0% |
| S17b; 21 h dry in 20 C. Bryair | 6.9% | 66 | 3 | 4.5% |
| S17c; 5 hr dry in LFH | 21.4% | 55 | 3 | 5.5% |
| S17d; 21 h dry in LFH | 9.9% | 84 | 1 | 1.2% |
| S17e; 45 h dry in LFH | 9.5% | 76 | 1 | 1.3% |
| S17f; 69 h dry in LFH | 9.5% | 77 | 4 | 5.2% |

These experiments had copious amounts of *Agrobacterium* overgrowth so we tried this set again with the GV3101 strain, adding in 400 mg/L carbenicillin to the selective soy B5 medium to better control overgrowth. Transformation metrics for this set are given in Table 9:

TABLE 9

Transformation metrics for Williams82 soybean VAE Batches S17a-f (GV3101/VS225)

| Treatment | Internal Moisture | # Explants | # T0 Plants | TF |
| --- | --- | --- | --- | --- |
| S17a; 5 h dry in 20 C. Bryair | 12.4% | 154 | 5 | 3.2% |
| S17b; 21 h dry in 20 C. Bryair | 6.9% | 97 | 1 | 1.0% |
| S17c; 5 hr dry in LFH | 21.4% | 96 | 4 | 4.2% |
| S17d; 21 h dry in LFH | 9.9% | 103 | 1 | 1.0% |
| S17e; 45 h dry in LFH | 9.5% | 94 | 7 | 7.6% |
| S17f; 69 h dry in LFH | 9.5% | 105 | 8 | 7.6% |

Figure 7:
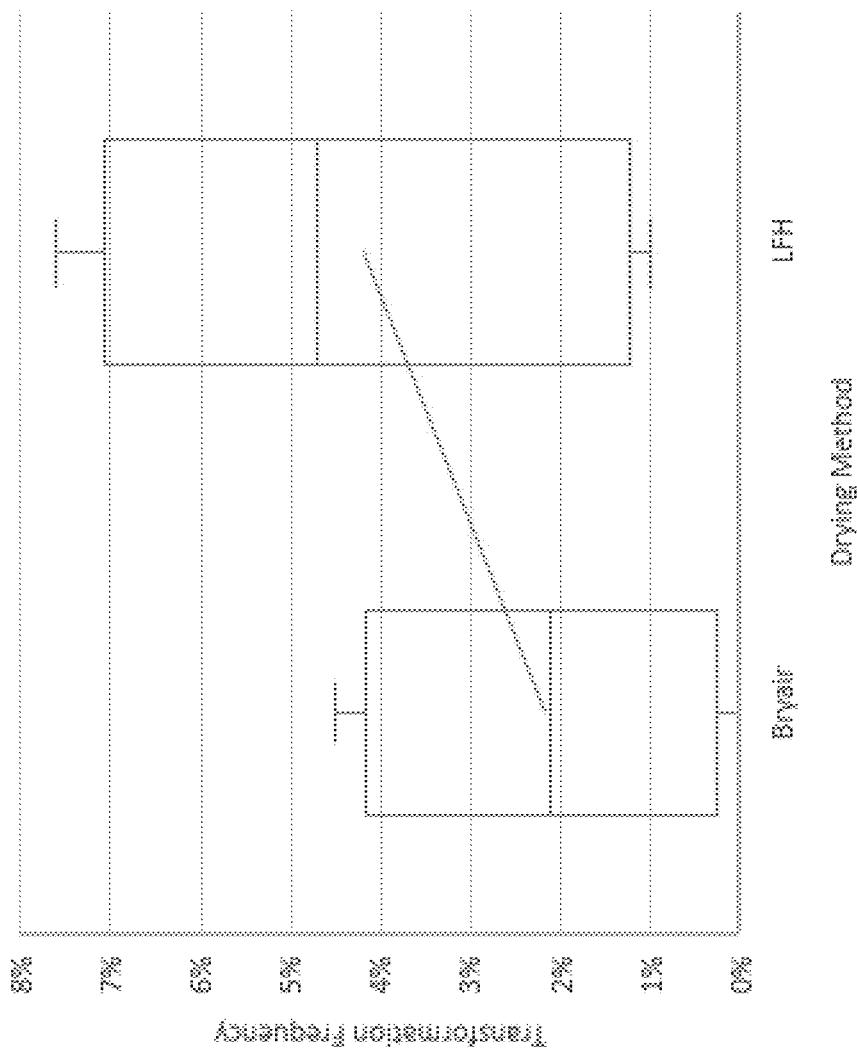
FIG. 7 shows transformation frequency and drying method in soybean VAEs.
Figure 8:
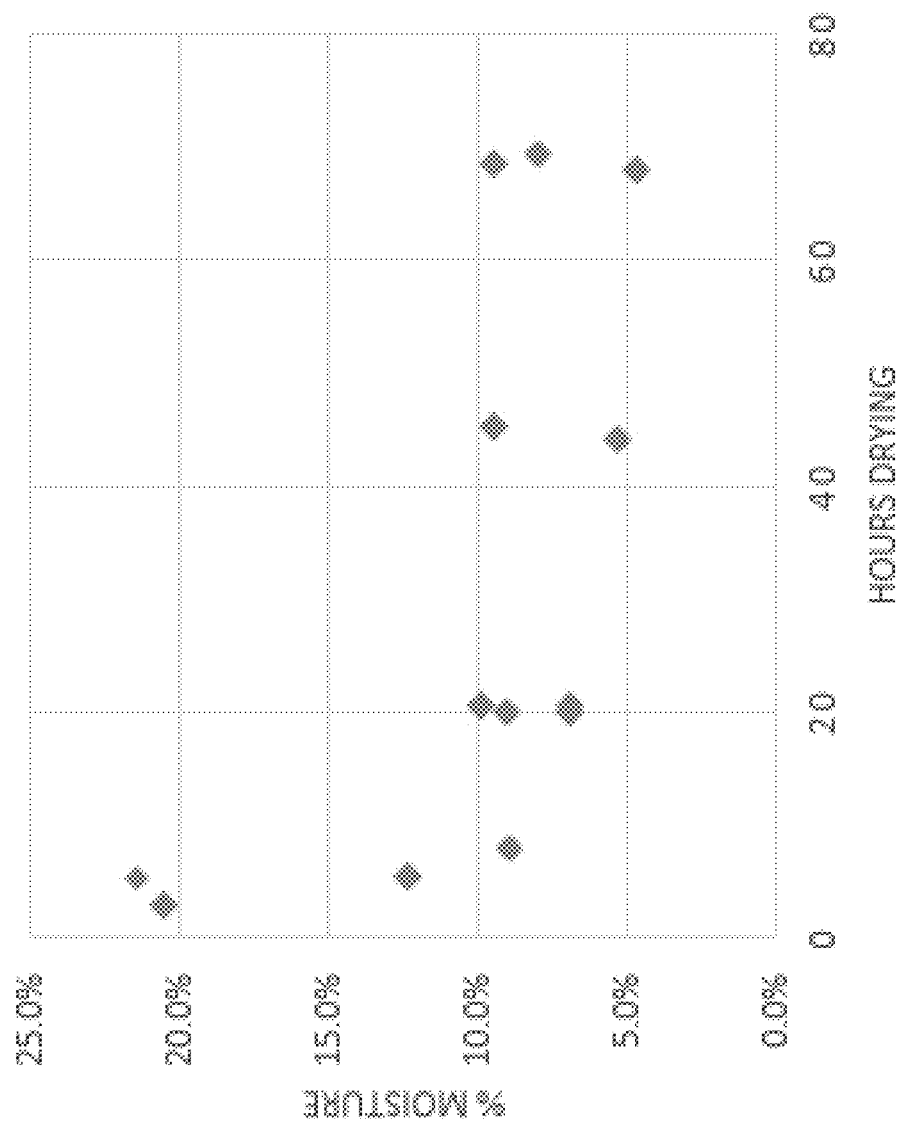
FIG. 8 shows rate of moisture decay in soybean VAEs dried in LFH vs. Bryair.

We noticed that combining these two data sets indicated an overall higher TF in soy VAEs dried in LFH for 5-69 hours (22 plants/539 explants; TF=4.1%) than soy VAEs dried in the 20 C Bryair for 5-21 hours (9 plants/364 explants; TF=2.5%) (FIG. 7). We believe this is due to a reduced rate of drying in the LFH VAEs relative to the Bryair dried Soy VAEs, where initial moisture prior to drying is approximately 65% (FIG. 8).

Prior to drying down the soy meristem explants giving rise to the VAE S17 series, we inoculated a small amount of them freshly excised and exposed some of them to TDZ in co-culture at 1 mg/L. We found an apparent benefit to this approach, as shown in Table 10.

TABLE 10

Transformation metrics for freshly excised Williams82 with and without TDZ in co-culture

| Treatment | # Explants | # T0 Plants | TF |
| --- | --- | --- | --- |
| Fresh sample of explants dried to generate S17 series | 85 | 4 | 4.7% |
| Fresh sample of explants dried to generate S17 series TDZ in co-culture | 95 | 12 | 12.6% |

We decided to use this combined strategy of optimized drying conditions (in the examples shown, limiting the time soybean explants were in the Bryair to 5-6 hours) and using TDZ in co-culture to transform elite genotypes other than Williams82. Transformation metrics for the LD10-30087, 30092, 30094 varieties are given in Table 11, and those for 3025N, 3849N, and Williams82 control are given in Table 12.

TABLE 11

Transformation metrics for soyben VAE batches of cultivars LD10-30087, 30092, and 30094 with and without TDZ in co-culture

| Treatment | Co-culture | Germplasm | # Explants | # T0 Plants | TF |
| --- | --- | --- | --- | --- | --- |
| S18; 6 h dry in 20 C. Bryair to 27% moisture | No TDZ | LD10-30087 | 26 | 0 | 0% |
| S19; 6 h dry in 20 C. Bryair to 21% moisture | No TDZ | LD10-30092 | 59 | 0 | 0% |
| S20; 6 h dry in 20 C. Bryair to 18% moisture | No TDZ | LD10-30094 | 99 | 0 | 0% |
| S18; 6 h dry in 20 C. Bryair to 27% moisture | TDZ | LD10-30087 | 74 | 1 | 1.4% |
| S19; 6 h dry in 20 C. Bryair to 21% moisture | TDZ | LD10-30092 | 91 | 3 | 3.3% |
| S20; 6 h dry in 20 C. Bryair to 18% moisture | TDZ | LD10-30094 | 85 | 1 | 1.2% |

TABLE 12

Transformation metrics for soybean VAE batches of cultivars 3025N, 3849N, and Williams82 with and without TDZ in co-culture

| Treatment | Co-culture | Germplasm | # Explants | # T0 Plants | TF |
| --- | --- | --- | --- | --- | --- |
| S16b; 5 h dry in 20 C. Bryair to 8.3% moisture | No TDZ | 3025N | 166 | 0 | 0% |
| S16b; 5 h dry in 20 C. Bryair to 8.3% moisture | TDZ | 3025N | 162 | 1 | 0.6% |
| S27; 5 h dry in 20 C. Bryair | No TDZ | 3849N | 350 | 7 | 2.0% |
| S27; 5 h dry in 20 C. Bryair | TDZ | 3849N | 289 | 6 | 2.1% |
| S26; 6 h dry in 20 C. Bryair | No TDZ | W82 | 189 | 5 | 2.6% |
| S26; 6 h dry in 20 C. Bryair | TDZ | W82 | 182 | 8 | 4.4% |

Figure 9:
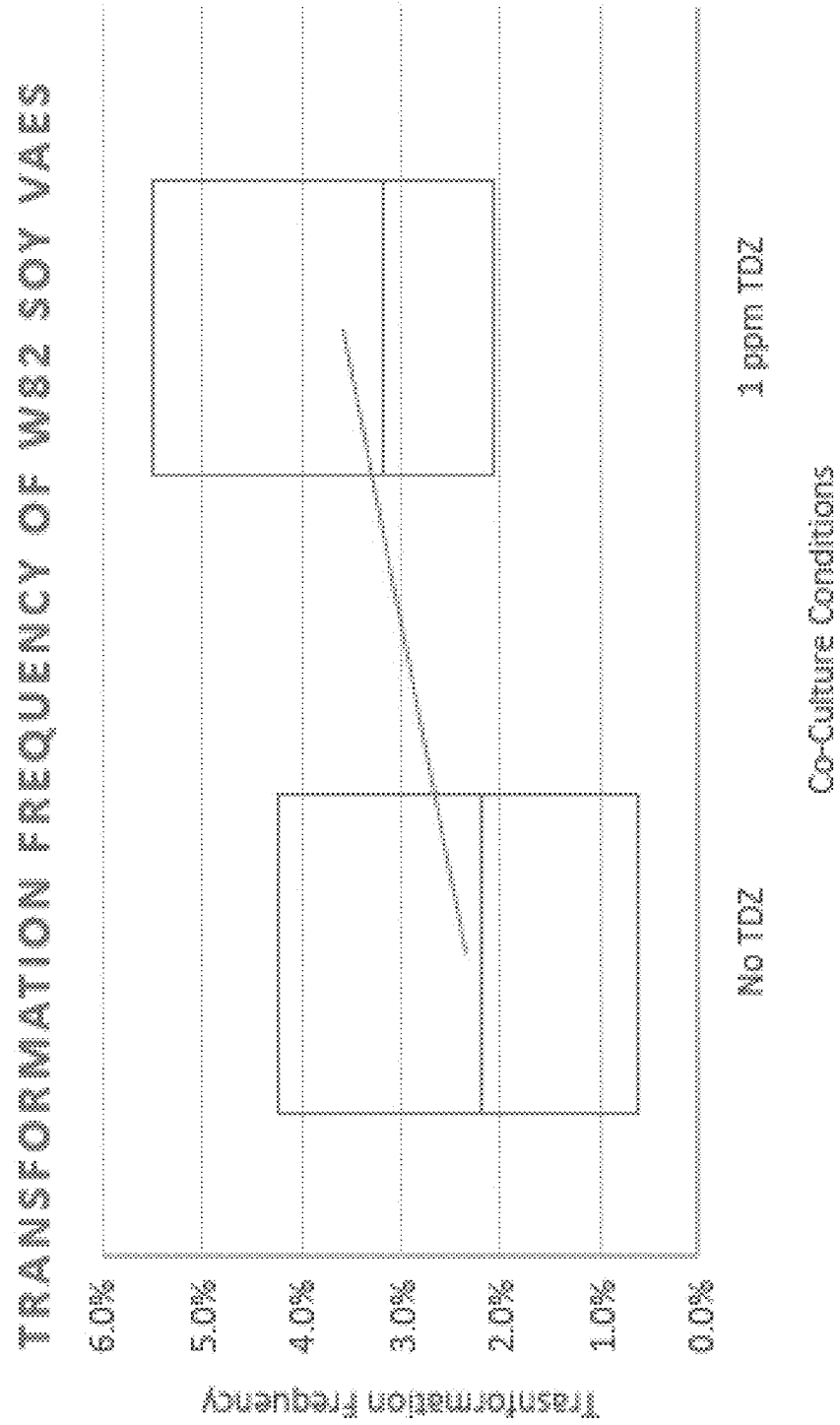
FIG. 9 shows transformation frequency of W82 soybean VAE batches with and without TDZ in co-culture.

Testing TDZ in co-culture was repeated two more times in W82 VAEs under different drying conditions. Table 13a summarizes this data, and is shown in boxplot form in FIG. 9. Experimental replicates are outlined in tables 13b and 13c.

TABLE 13a

Transformation frequency of W82 Soy VAE batches with and without TDZ in co-culture

| Germplasm | Drying Conditions | Co-Culture | # Explants | # R0 Plants | TF |
|---|---|---|---|---|---|
| W82 | various | No TDZ | 437 | 11 | 2.5% |
| W82 | various | 1 ppm TDZ | 452 | 17 | 3.8% |

TABLE 13b

First set of experimental replicates for W82 soybean VAEs

| Germplasm | Drying Conditions | Co-Culture | # Explants | # T0 Plants | TF |
|---|---|---|---|---|---|
| W82 | 20 C. Bryair 6 h | No TDZ | 189 | 8 | 4.2% |
| W82 | 20 C. Bryair 6 h | 1 ppm TDZ | 182 | 10 | 5.5% |

TABLE 13c

Second set of experimental replicates for W82 soybean VAEs

| Germplasm | Drying Conditions | Co-Culture | # Explants | # T0 Plants | TF |
|---|---|---|---|---|---|
| W82 | LFH 20.5 h | No TDZ | 157 | 1 | 0.6% |
| W82 | LFH 20.5 h | 1 ppm TDZ | 144 | 3 | 2.1% |
| W82 | 20 C. Bryair 5.5 h | No TDZ | 91 | 2 | 2.2% |
| W82 | 20 C. Bryair 5.5 h | 1 ppm TDZ | 126 | 4 | 3.2% |

Figure 10:
FIG. 10 shows a GUS+ R0 event from particle-mediated transformation of soybean VAE.

We extended the transformation capability of soybean VAEs to particle bombardment and found we could recover R0 plants. FIG. 10 gives the first soybean R0 event from VAEs through particle bombardment, and Table 14 gives initial transformation metrics.

TABLE 14

Transformation metrics for pilot Particle Bombardment work (VS225 DNA) using Soy VAEs

| Treatment | DNA Loading Rate (ng DNA/ug gold) | Drying Conditions | Germplasm | # Explants | # T0 Plants | TF |
|---|---|---|---|---|---|---|
| Particle Gun; 1350 psi, 6 cm | 1.2 | 5.5 h 20 C. Bryair | W82 | 180 | 3 | 1.7% |
| Particle Gun; 1350 psi, 6 cm | 1.2 | 19 h 20 C. Bryair | Single seed descent W82 | 96 | 3 | 3.1% |

Figure 11:
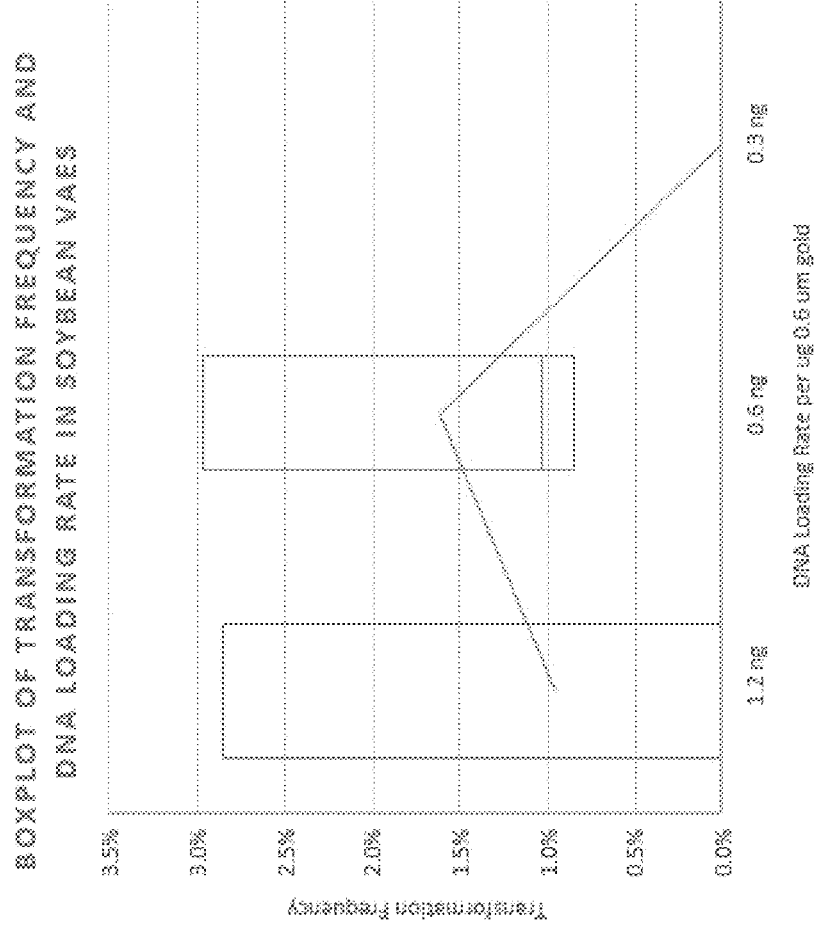
FIG. 11 shows transformation metrics for Particle Bombardment work (VS225 DNA) using soybean VAEs varying DNA loading rate.

We varied the DNA loading rate on beads and testing in soybean VAE transformation, and results are given in Table 15a. These results suggest we can reduce the amount of DNA loaded onto gold while still maintaining TF. This may enable us to increase quality plant production by reducing multiple copy events. Data demonstrating the transformation frequency based on DNA loading rate is shown in FIG. 11.

Table 15a: Transformation metrics for particle bombardment work (VS225 DNA) using soybean VAEs and varying DNA loading rate TABLE 15b First set of experimental replicates for soybean VAE DNA loading

| Treatment | DNA Loading Rate (ng DNA/ ug gold) | Germplasm | # Explants | # T0 Plants | TF |
|---|---|---|---|---|---|
| Particle Gun; 1350 psi, 6 cm | 1.2 | W82 | 79 | 0 | 0.0% |
| Particle Gun; 1350 psi, 6 cm | 0.6 | W82 | 101 | 3 | 3.0% |

TABLE 15c

Second set of experimental replicates for soybean VAE DNA loading

| Treatment | DNA Loading Rate (ng DNA/ ug gold) | Germplasm | # Explants | # T0 Plants | TF |
|---|---|---|---|---|---|
| Particle Gun; 1350 psi, 6 cm | 1.2 | W82 | 99 | 0 | 0.0% |
| Particle Gun; 1350 psi, 6 cm | 0.6 | W82 | 97 | 1 | 1.0% |
| Particle Gun; 1350 psi, 6 cm | 0.3 | W82 | 79 | 0 | 0.0% |

TABLE 15d

Third set of experimental replicates for soybean VAE DNA loading

| Treatment | DNA Loading Rate (ng DNA/ ug gold) | Germplasm | # Explants | # T0 Plants | TF |
|---|---|---|---|---|---|
| Particle Gun; 1350 psi, 6 cm | 1.2 | W82 | 35 | 1 | 2.9% |
| Particle Gun; 1350 psi, 6 cm | 0.6 | W82 | 117 | 1 | 0.9% |
| Particle Gun; 1350 psi, 6 cm | 0.3 | W82 | 60 | 0 | 0.0% |

Figure 12:
FIG. 12 shows GFP+ shoot clearly originates from axil. Second axil is GFP−. Taller shoot GFP−.
Figure 13:
FIG. 13 shows SAM apparently missing. RFP+ Shoot from AM

We tracked the ontogeny of the shoots using binaries expressing either GFP or RFP and found the majority of transgenic shoots originated from axillary meristems (AM) rather than the shoot apical meristem (SAM). As shown in FIG. 12, the GFP positives shoots originate from axial meristem whereas the SAM is GFP negative. Taller shoots are also GFP negative. In FIG. 13, the SAM is missing, but both shoots from the AM are RFP positive.

Figure 14:
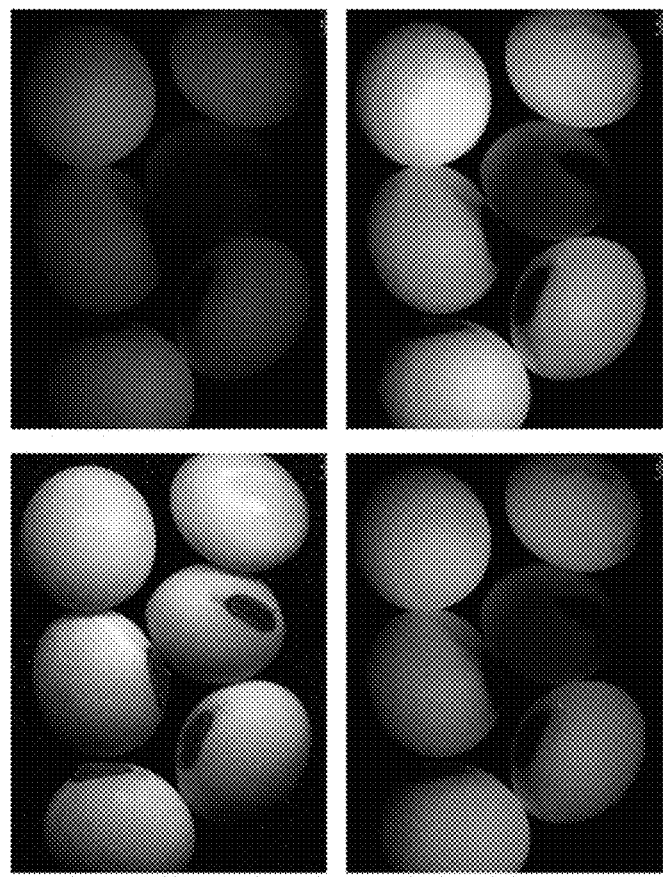
FIG. 14 shows RFP expression in segregating T1 soybean seed of VAE event WP332-1 (single seed descent W82+ pWI-1000 dsRED); VAE dried in Bryair 20 C for 6 h; TDZ in co-culture (light intensity increased in sequential panels).
Figure 15:
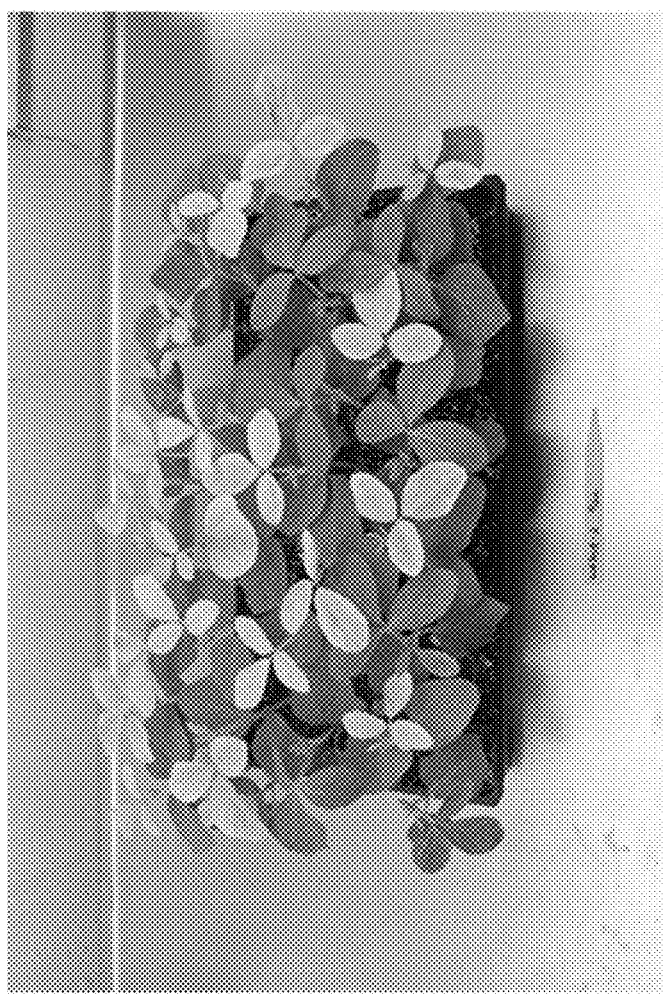
FIG. 15 shows aadA expression in segregating T1 soybean plants of VAE event WP308-2 (single seed descent W82+VS225); VAE dried in Bryair 20 C for 19 h; TDZ in pre-culture and resting phase pre- and post-bombardment. Imaged 6 days after spraying with 1000 ppm spectinomycin; sprayed 10 days after planting.
Figure 16:
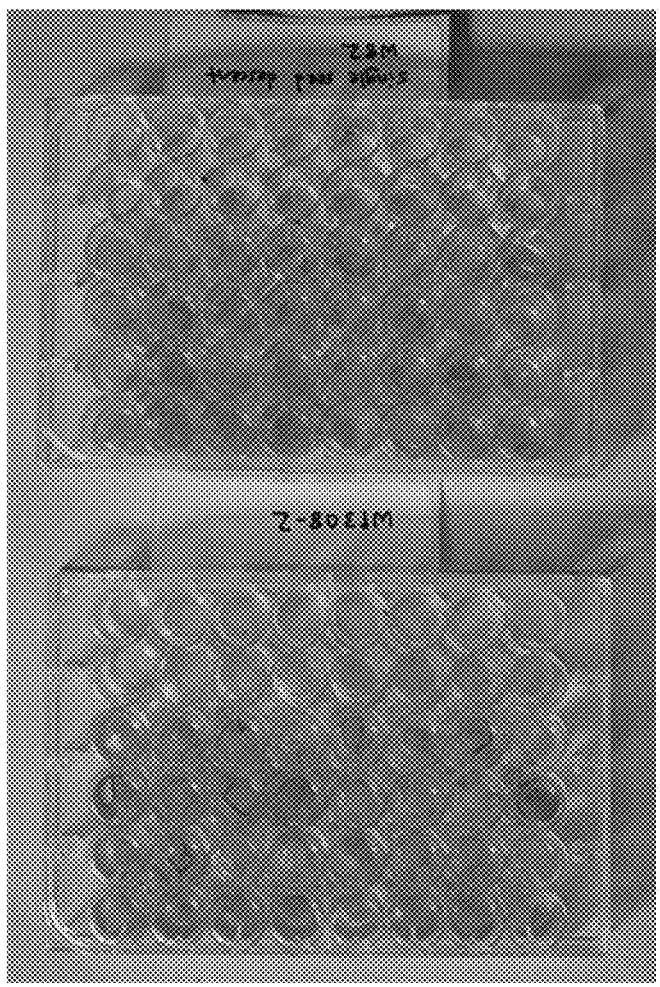
FIG. 16 shows GUS expression in segregating T1 Soybean leaf samples of VAE event WP308-2 (single seed descent W82+VS225, on left); VAE dried in Bryair 20 C for 19 h; TDZ in pre-culture and resting phase pre- and post-bombardment. Control leaves on right. Sampled 10 days after planting.

Soybean VAEs are a storable, shippable explant that can be used to transform multiple genotypes. They represent a collaboration tool across multiple research sites. We have also demonstrated transmission of the dsRED transgene into T1 progeny of events derived from Soybean VAEs (FIG. 14). We have also demonstrated transmission of gus and aadA transgenes in both particle-mediated and *Agrobacterium*-mediated transformation of soybean VAEs (particle-mediated results shown in FIGS. 15 and 16). T1 date for soybean VAE transformations is summarized in Table 16.

Figure 17:
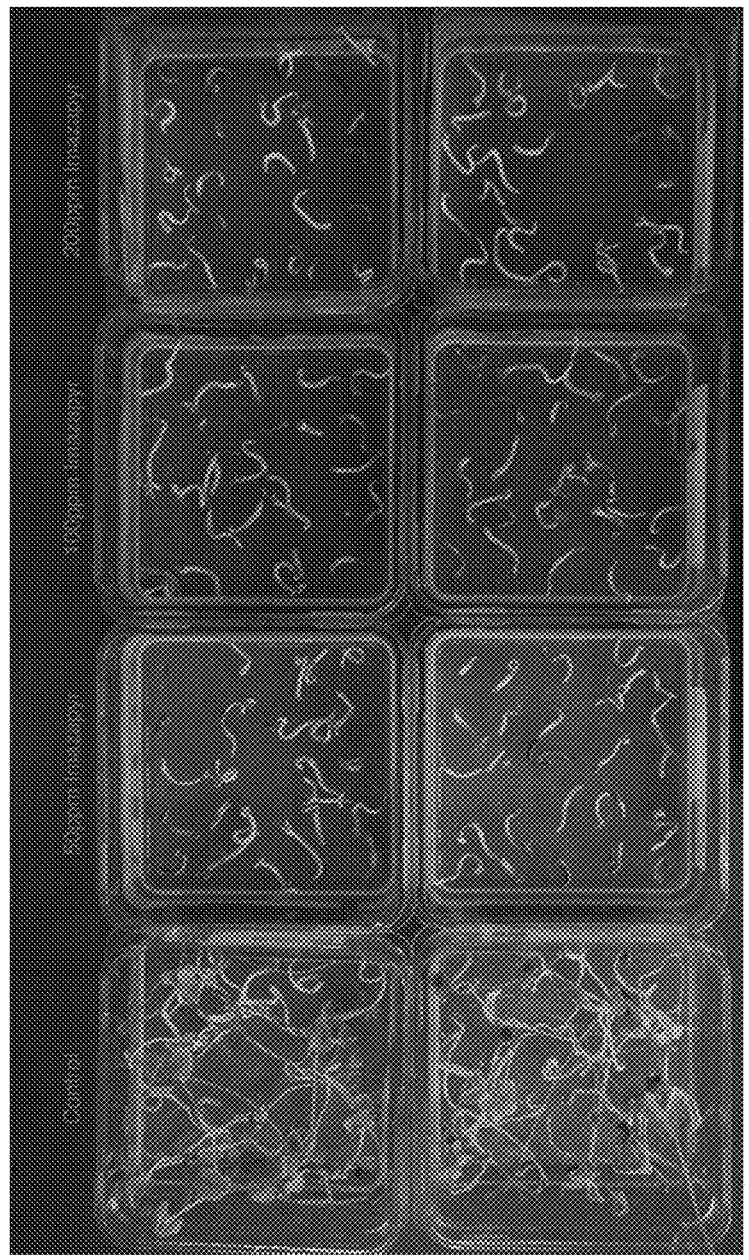
FIG. 17 shows imazapyr selection titration at 5 weeks using W82 Soybean VAEs.
Figure 18:
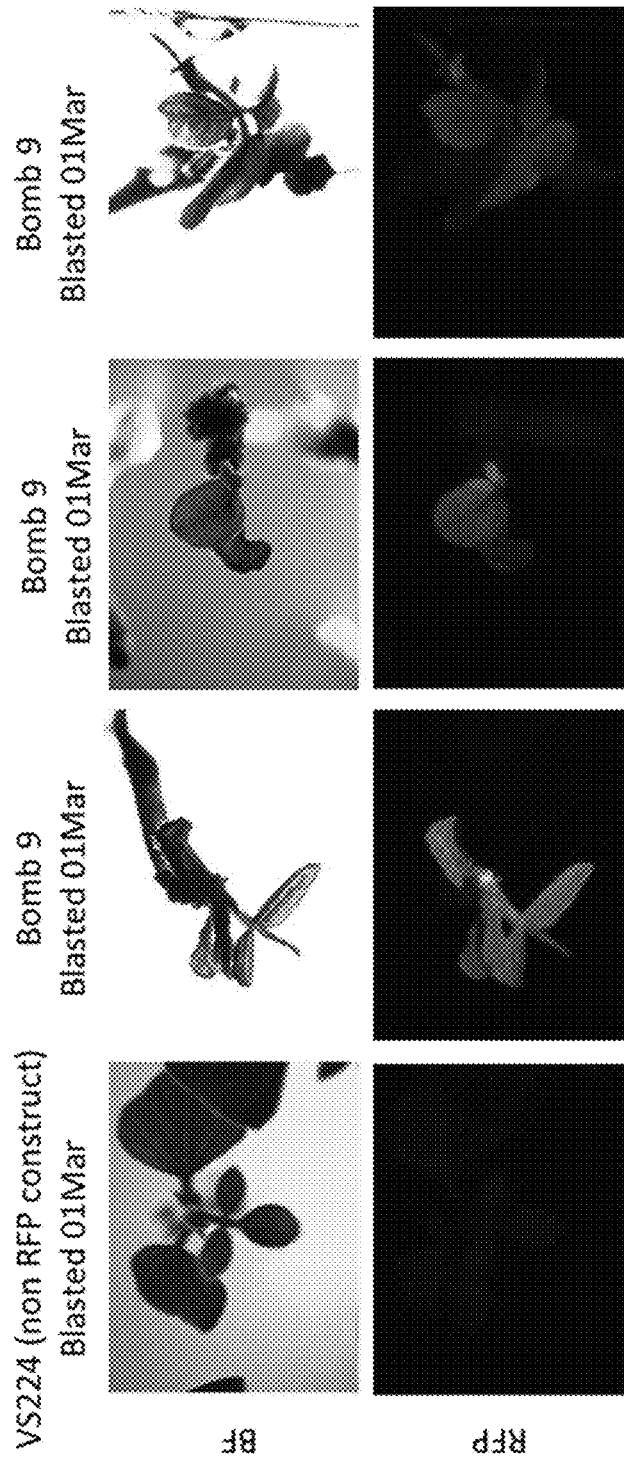
FIG. 18 shows stable RFP expression in putative Soybean events on glyphosate selection (3 weeks post-bombardment).
Figure 19:
FIG. 19 shows stable RFP activity in soybean Williams82 shoots derived from VAEs bombarded with pWI-1000 dsRED.

It may be possible to use alternate selectable markers in the Soybean VAE transformation system. FIG. 17 shows non-transformed soybean VAEs exposed to different levels of imazapyr, and FIG. 18 shows stable RFP activity in soybean events generated from particle-mediated transformation with glyphosate selection.

Approximately 32 T1 progeny seed from 31 soybean events were planted in the greenhouse to test for transmission of transgene. These events were generated from our current VAE drying process, which consists in drying soybean VAEs under generally mild conditions (examples of mild conditions given in Table 17 in the bold italicized rows).

TABLE 17

Soybean VAE drying conditions (standard process in bold italics)

| Soy VAE Drying Method | Drying Duration (hours) | Internal Moisture | Batch Assayed |
|---|---|---|---|
| Bryair (30 C., non-humidity controlled) | 20 | 4.5% | S13 |
| Bryair (30 C., non-humidity controlled) | 72 | 3.2% | S8 |
| *Bryair (20C, non-humidity controlled)* | *5* | *12.4%* | *S17A* |
| Bryair (20 C., non-humidity controlled) | 21 | 6.9% | S17B |
| *Bryair (20C, humidity controlled)* | *24* | *11.1%* | *S82* |
| Laminar Flow Hood = LFH | 5 | 21.4% | S17C |
| *LFH* | *21* | *9.9%* | *S17D* |
| LFH | 45 | 9.5% | S17E |
| LFH | 69 | 9.5% | S17F |

Approximately one week later, seedlings were imaged, leaves sampled for GUS, leaves imaged for RFP (if applicable), and whole plants sprayed with 1000 mg/L spectinomycin. Plants were then imaged again approximately 5-6 days later.

TABLE 16

T1 Soybean Data from VAE Transformation

| WP Plant ID | Method | Construct | Gus Positive T1 Cotyledons | Gus Negative T1 Cotyledons | Gus Positive Seed Coats | Number of T1 Seeds Tested | % Gus Positive T1 | % Resistant to Spec 1000 Spray T1 | % RFP Positive T1 |
|---|---|---|---|---|---|---|---|---|---|
| WP307-3 | Spec Particles | VS225 (particle gun) | 0 | 8 | 0 | 8 | 0.0% | NA | NA |
| WP307-4 | Spec Particles | VS225 (particle gun) | 5 | 3 | 5 | 8 | 62.5% | NA | NA |
| WP307-10 | Spec Particles | VS225 (particle gun) | 1 | 6 | 7 | 7 | 14.3% | NA | NA |
| WP307-11 | Spec Particles | VS225 (particle gun) | 5 | 3 | 8 | 8 | 62.5% | NA | NA |
| WP307-12 | Spec Particles | VS225 (particle gun) | 6 | 2 | 0 | 8 | 75.0% | NA | NA |
| WP308-2 | Spec Particles | VS225 (particle gun) | 4 | 4 | 8 | 8 | 50.0% | NA | NA |
| WP308-3 | Spec Particles | VS225 (particle gun) | 7 | 1 | 8 | 8 | 87.5% | NA | NA |
| 200001-1 D2 (12) | AGL1 | VS225 | | | | 32 | 56.0% | 56.0% | NA |
| WP300-36 | GV3101 | VS225 | | | | 32 | 13.0% | 0.0% | NA |
| WP300-38 | GV3101 | VS225 | | | | 32 | 53.0% | 38.0% | NA |
| WP303-6 | GV3101 | VS225 | | | | 29 | 59.0% | 59.0% | NA |
| WP305-4 | GV3101 | VS225 | | | | 32 | 72.0% | 59.0% | NA |
| WP306-7 | GV3101 | VS225 | | | | 25 | 76.0% | 64.0% | NA |
| WP308-2 | Spec Particles | VS225 (particle gun) | | | | 31 | 35.0% | 26.0% | NA |
| WP332-1 | GV3101 | pWI-1000 dsRED | | | | 32 | 75.0% | 88.0% | 88.0% |

Figure 28:
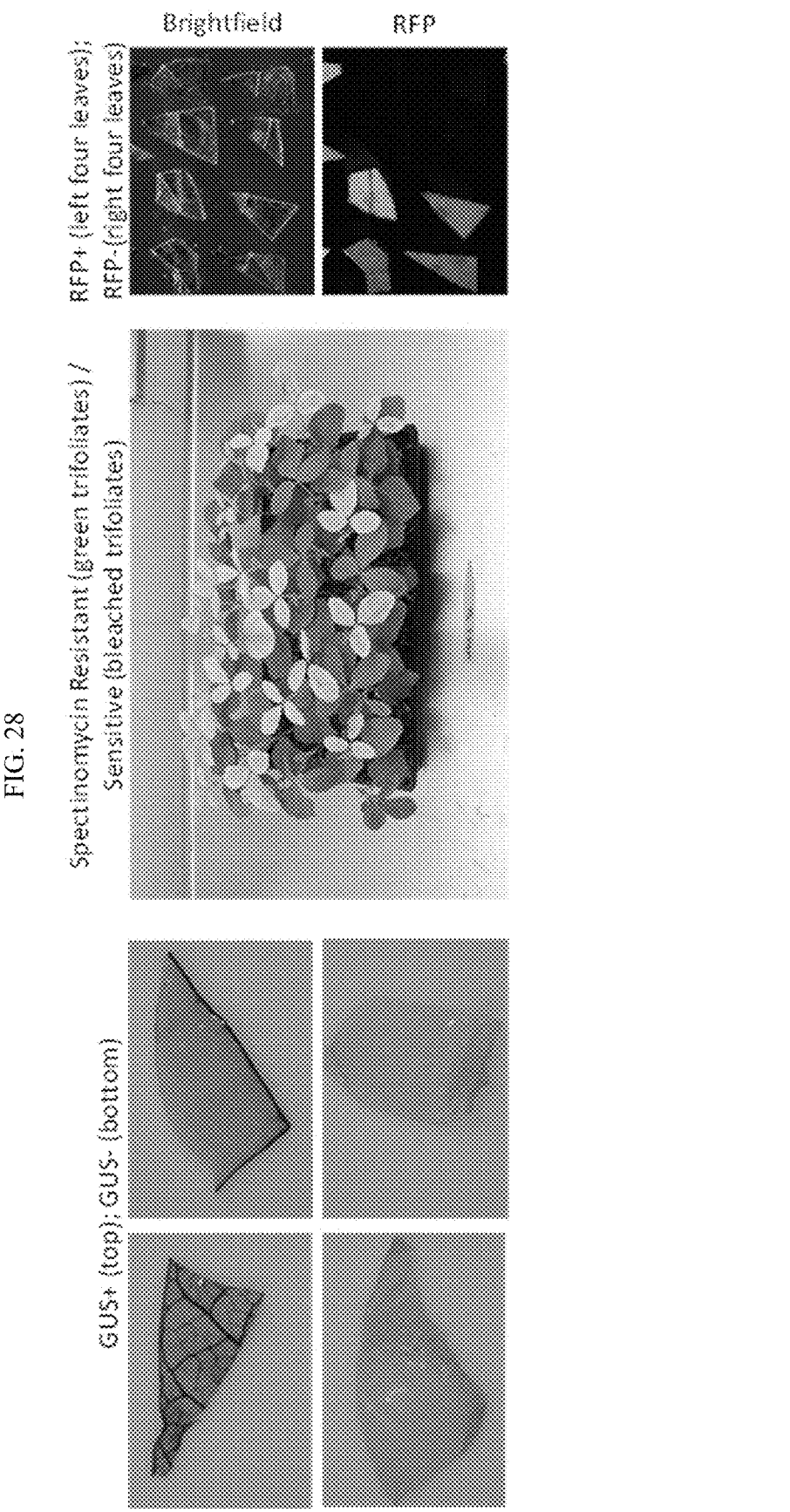
FIG. 28 shows GUS, aadA, and RFP Expression in T1 Soybean.
Figure 30:
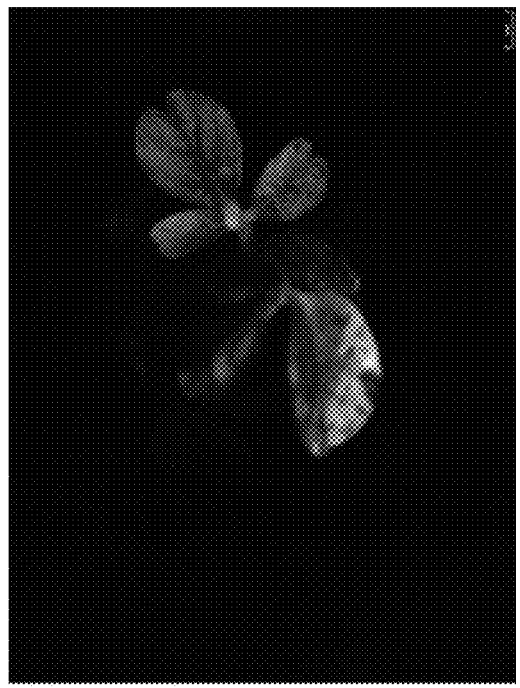
FIG. 30 shows stable RFP Activity in soybean shoot regenerated from VAE bombarded with Bomb 9.
Figure 30:
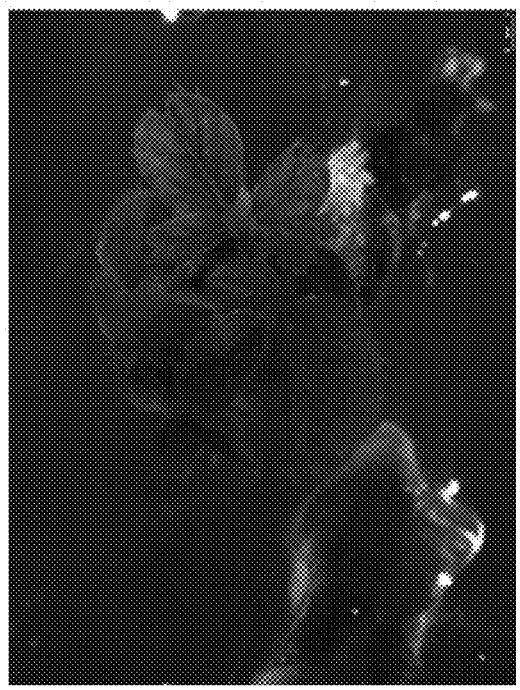
Figure 31:
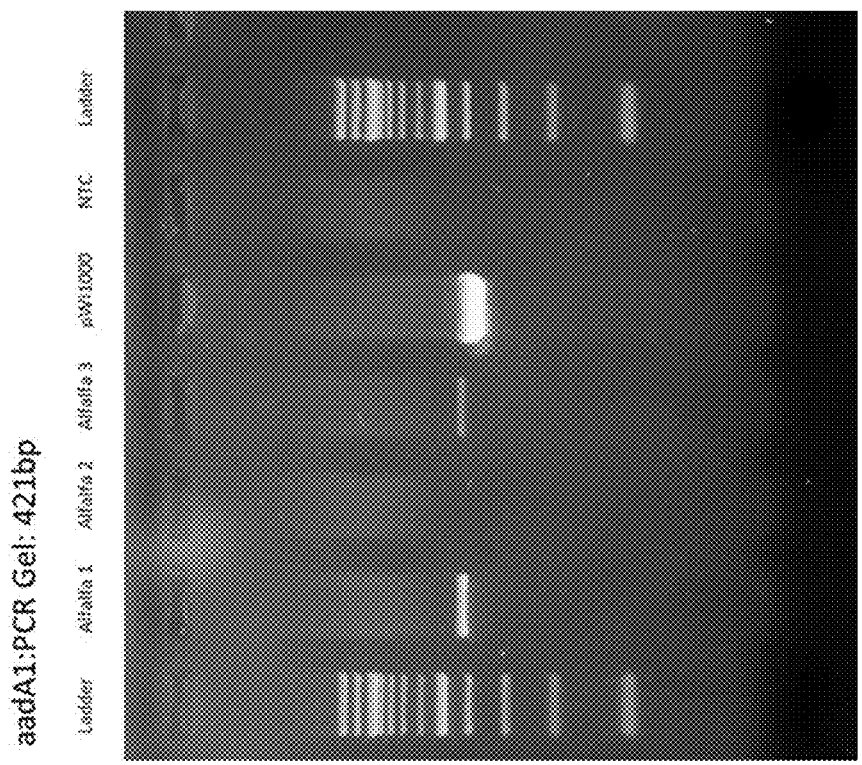
FIG. 31 shows PCR results of T0 transgenic alfalfa events generated from meristem explants.
Figure 32:
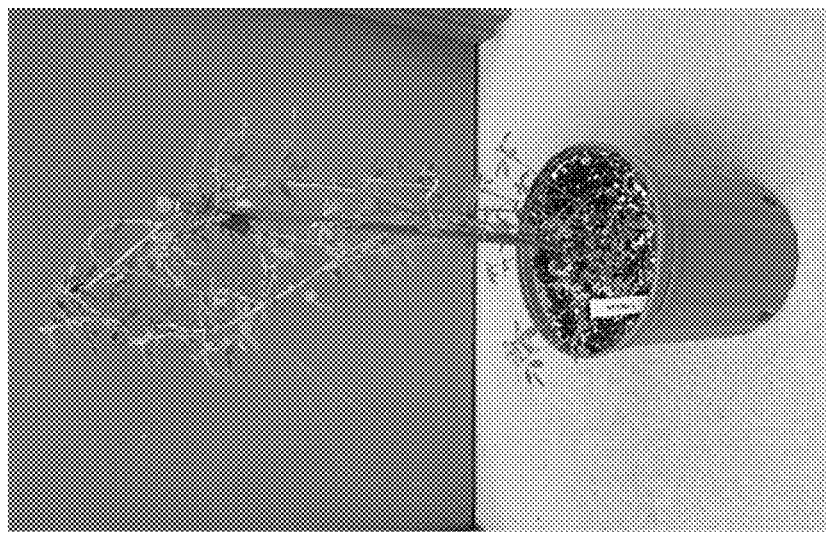
FIG. 32 shows transgenic alfalfa T0 event WP350-1 imaged ~7 weeks in greenhouse.

Examples of GUS+, RFP+ and spec resistant plants are given in FIG. 28, and summary of transgene transmission in given in Table 18. Out of the 31 transgenic soy lines tested, 25 (81%) produced transgenic T1 seed that were positive for all transgenic protein products tested.

work focused on reducing this cytokinin load during the preculture/rest phase. The T0 rooted shoots tested positive for GUS and RFP (tdTomato). FIG. 30 shows stable RFP activity in soybean shoot regenerated from VAE bombardment with Bomb 9.

TABLE 18

Transmission of transgenes in soybean events derived from meristem explants

| T0 Plant ID | Germplasm | Explant Excision | Construct | Transformation method | # T1 Seedlings Assayed | GUS leaf expression % T1 POS | Spectinomycin spray phenotype % T1 Resistant | RFP (dsRED) % T1 POS |
|---|---|---|---|---|---|---|---|---|
| 200001-1 D2 (12) | W82 | hand | VS225 | Agrobacterium | 32 | 56% | 56% | n/a |
| WP300-36 | W82 | machine | VS225 | Agrobacterium | 32 | 13% | 0% | n/a |
| WP300-38 | W82 | machine | VS225 | Agrobacterium | 32 | 53% | 38% | n/a |
| WP308-2 | single seed descent W82 | machine | VS225 | particle gun | 31 | 35% | 26% | n/a |
| WP332-1 | single seed descent W82 | machine | pWI-1000 dsRED | Agrobacterium | 32 | 75% | 88% | 88% |
| WP303-6 | LD1030092 | machine | VS225 | Agrobacterium | 29 | 59% | 59% | n/a |
| WP305-4 | 3025N | machine | VS225 | Agrobacterium | 32 | 72% | 59% | n/a |
| WP306-7 | 3849N | machine | VS225 | Agrobacterium | 25 | 76% | 64% | n/a |
| WP300-30 | W82 | machine | VS225 | Agrobacterium | 29 | 38% | 28% | n/a |
| WP300-32 | W82 | machine | VS225 | Agrobacterium | 30 | 80% | 57% | n/a |
| WP300-31 | W82 | machine | VS225 | Agrobacterium | 11 | 0% | 0% | n/a |
| WP306-4 | 3849N | machine | VS225 | Agrobacterium | 13 | 8% | 8% | n/a |
| WP300-33 | W82 | machine | VS225 | Agrobacterium | 31 | 39% | 32% | n/a |
| WP301-3 | single seed descent W82 | machine | VS225 | Agrobacterium | 31 | 94% | 97% | n/a |
| WP306-1 | 3849N | machine | VS225 | Agrobacterium | 22 | 86% | 82% | n/a |
| WP306-2 | 3849N | machine | VS225 | Agrobacterium | 3 | 33% | 33% | n/a |
| WP306-3 | 3849N | machine | VS225 | Agrobacterium | 30 | 53% | 50% | n/a |
| WP306-10 | 3849N | machine | VS225 | Agrobacterium | 30 | 73% | 80% | n/a |
| WP306-11 | 3849N | machine | VS225 | Agrobacterium | 32 | 0% | 0% | n/a |
| WP303-4 | LD10-30092 | machine | VS225 | Agrobacterium | 28 | 0% | 64% | n/a |
| WP303-5 | LD10-30092 | machine | VS225 | Agrobacterium | 6 | 17% | 17% | n/a |
| WP300-48 | W82 | machine | VS225 | Agrobacterium | 29 | 44% | 38% | n/a |
| WP300-53 | W82 | machine | VS225 | Agrobacterium | 30 | 30% | 23% | n/a |
| WP300-54 | W82 | machine | VS225 | Agrobacterium | 24 | 0% | 0% | n/a |
| WP300-77 | W82 | machine | VS225 | Agrobacterium | 26 | 69% | 46% | n/a |
| WP331-17 | W82 | machine | pWI-1000 | Agrobacterium | 25 | 48% | 28% | n/a |
| WP331-19 | W82 | machine | pWI-1000 | Agrobacterium | 27 | 56% | 59% | n/a |
| WP337-1 | 3849N | machine | pWI-1000 | Agrobacterium | 31 | 39% | 71% | n/a |
| WP337-2 | 3849N | machine | pWI-1000 | Agrobacterium | 31 | 0% | 0% | n/a |
| WP337-3 | 3849N | machine | pWI-1000 | Agrobacterium | 32 | 78% | 78% | n/a |
| WP337-4 | 3849N | machine | pWI-1000 | Agrobacterium | 32 | 3% | 69% | n/a |
| Neg Control | W82 | n/a | n/a | n/a | 64 | 0% | 0% | n/a |
| Neg Control | single seed descent W82 | n/a | n/a | n/a | 32 | 0% | 0% | 0% |
| Neg Control | LD10-30092 | n/a | n/a | n/a | 40 | 0% | 0% | n/a |
| Neg Control | 3849N | n/a | n/a | n/a | 49 | 0% | 0% | n/a |
| Neg Control | 3025N | n/a | n/a | n/a | 30 | 0% | 0% | n/a |

Figure 29:
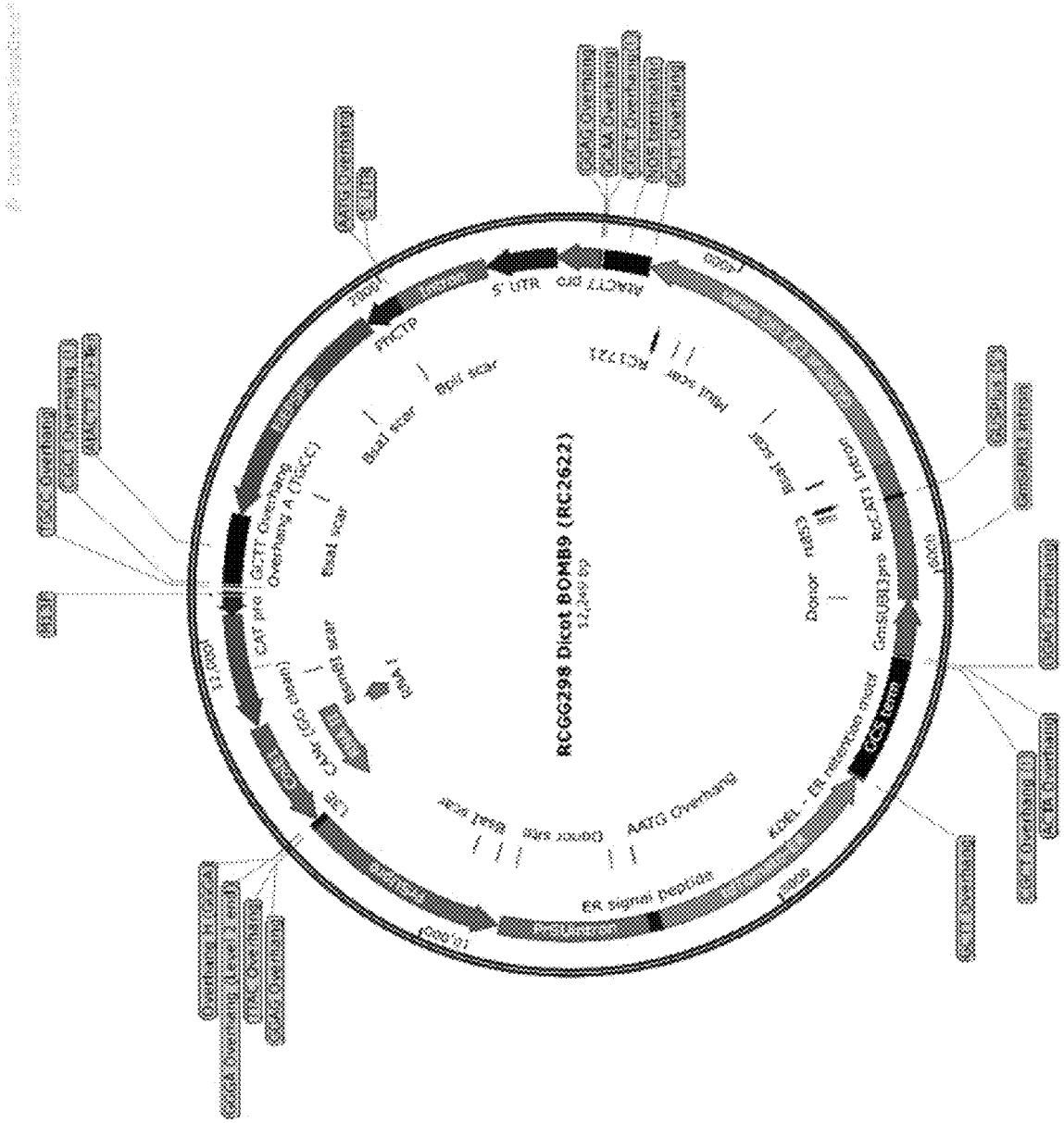
FIG. 29 shows a plasmid mad of Dicot Bomb 9 used in glyphosate selection methods.

Alternate selectable markers for soybean VAE transformation—We applied soybean VAE technology to glyphosate selection, and were able to recover T0 plants from particle bombardment using Dicot Bomb 9 (FIG. 29) and the Goosegrass EPSP; where the explants were selected on 75 uM glyphosate; then rooted on 25 uM glyphosate. We found that the preculture and resting media conditions used with particle bombardment/spectinomycin selection yielded no plants with glyphosate selection, possibly because of cytokinin-like activity of glyphosate (through its inhibition of tryptophan and downstream auxin) negatively interacting with TDZ in these medias (EJW1). Our glyphosate selection

TABLE 19

Summary of experiments yielding positive T0 plants (all with 0.6 μm gold beads at 0.6 ng DNA/mg gold; 1350 psi at 6 cm) with BOMB 9

| Preculture Media | Rest media | Initial Explants | Rooting Shoots | TF |
|---|---|---|---|---|
| EJW1 (1 ppm TDZ) | EJW0 (no PGRs) | 264 | 1 | 0.4% |
| EJW3 (0.5 ppm TDZ) | EJW3 (0.5 ppm TDZ) | 387 | 2 | 0.5% |
| OR (3 ppm BAP) | OR (3 ppm BAP) | 380 | 1 | 0.3% |

REFERENCES 1. seednet.ap.nic.in/Stl/htmlpages/seedmoisturetesting.htm
2. Trick, H. N., and Finer, J. J. (1997) *Transgenic Research* 6, 329-336.
3. McCabe, D. E., Swain, W. F., Martinell, B. J., Christou, P. (1988) *Nature Biotechnology* 6(8), 923-926.
4. Chen, Y., Rivlin, A. Lange, A., Ye, X., Vaghchhipawala, Z., Eisinger, E., Dersch, E., Paris, M., Martinell, B., Wan, Y. (2014) *Plant Cell Reports* 33(1), 153-164.
5. Ye, X., Williams, E. J., Shen, J., Johnson, S., Lowe, B., Radke, S., Strickland, S. Esser, J. A., Petersen, M. W., and Gilbertson, L. A. (2011) *Transgenic Research* 20(4), 773-786.

Example 2

We have also obtained transient expression in meristematic region of dry bean explants hand excised, dried in LFH for 3 days, and inoculated with AGL1/VS225 and sonicated for 2 min 45 kHz after ~2 weeks storage at −20 C. We believe it is possible to optimize this transformation system to accommodate mechanically isolated dry bean meristem explants as well.

Example 3

We have also obtained transient GUS activity in freshly excised alfalfa explants hand excised from seed treated under a number of conditions.

Figure 24:
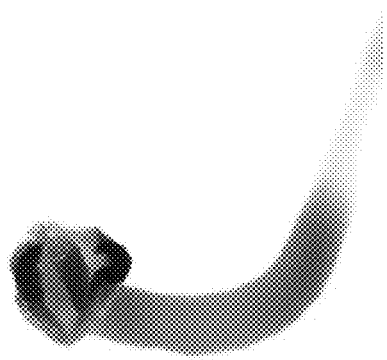
FIG. 24 shows alfalfa meristem transformation. Seeds were pre-cultured on B5 for 2 days; meristem explant were hand-excised; inoculated with GV3101/pWI-1000; 5 min 45 kHz; 4 day co-cultured in 2.5 ml WCIC INO (left). See germinated in GGM overnight; meristem explant hand-excised; inoculated with GV3101/pWI-1000; 5 min 45 kHz sonication; 4 day co-culture in 2.5 ml WCIC INO (right).

Alfalfa seeds of the Excelsior variety were surface sanitized in 70% ethanol for 10 minutes, rinsed 5× with sterile RO water, and then primed by allowing them to sit for 2 hrs at room temperature. Seeds were then imbibed in WCIC Bean Germination Media (BGM) overnight. Meristem explants were prepared the next day by removing seed coats and the majority of the cotyledonary tissue from the seed using a manual process under microscope. Meristem explants were then inoculated fresh. For use in transformation, alfalfa explants were incubated 1-2 hours at room temperature in 20% PEG4000 (dissolved in sterile distilled water) supplemented with 60 mg/L Captan fungicide and 30 mg/L Bravo (Daconil) fungicide. Explants were then rinsed 5-6× with sterile distilled water and inoculated with *Agrobacterium* strain GV3101 harboring the previously disclosed pWI-1000 binary. FIG. 24 shows transient activity in meristem of alfalfa explants after co-culture with *Agrobacterium*.

Meristem explants were inoculated under laminar flow in inverted PlantCon® and sonicated for 10 minutes, 45+/−2 kHz in a 0.1% Triton X-100 water bath. Inoculated explants were incubated with inoculum for additional 30 min at room temperature at 75 RPM. Excess inoculum was then removed, and explants co-cultured in PlantCons® with 2.5 ml WCIC INO media supplemented with 50 mg/L nystatin, 10 mg/L TBZ, and 95 uM lipoic acid at 23 C 16/8 photoperiod. This co-culture media was further supplemented with 1 mg/L TDZ in attempt to multiply meristematic cells and possibly suppress apical dominance. In some experiments acetosyringone was added to inoculum at 100 uM to help induce the vir operon.

Figure 27:
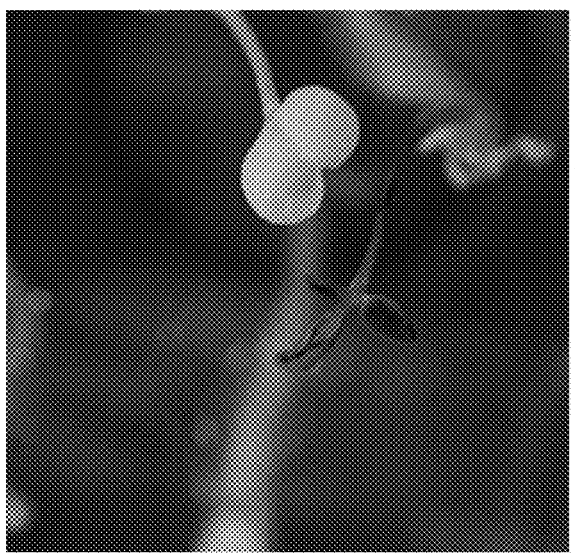
FIG. 27 shows an alfalfa shoot on 50 ppm spectinomycin.

After co-culture (3 days) explants were transferred to 50 ppm spectinomycin WCIC B5 media. When using the GV3101 strain we supplemented this selection media with 200-400 mg/L carbenicillin to knock *Agrobacterium* overgrowth down. Explants were transferred to fresh selection media as needed based on overgrowth (generally every 5-6 weeks for GV3101). Shoots from spectinomycin resistant plantlets were harvested and rooted on non-selective WCIC Bean Rooting Media (BRM) after being dipped in 1000 mg/L IAA. Rooted plants were sent to greenhouse for T1 seed set. A greening, spectinomycin-resistant alfalfa shoot erupting from axillary meristematic tissue is shown in FIG. 27 alongside a bleaching, spectinomycin-sensitive alfalfa explant.

From the pilot test, we recovered three alfalfa events from 99 meristem explants and sent them to greenhouse 5 months after inoculation. Alfalfa event 1 tested positive for the aadA transgene and was designated WP350-1. Alfalfa event 2 tested negative for the aadA transgene and was designated WP350-2. Alfalfa event 3 tested positive for the aadA transgene but did not survive the transition to greenhouse.

Example 4

Figure 25:
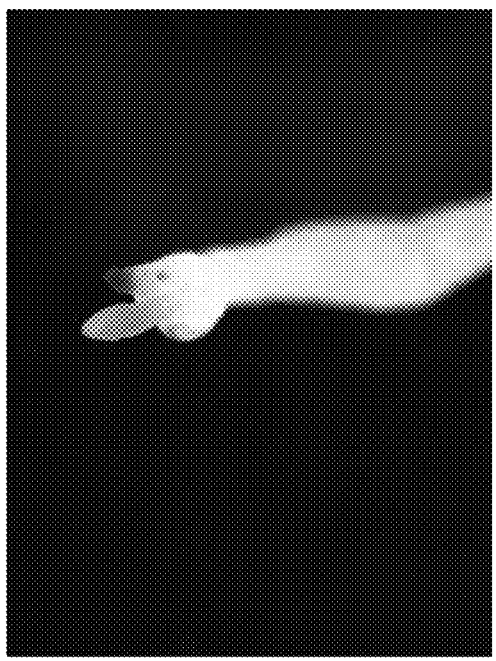
FIG. 25 shows transient GUS activity in cucumber meristem explant (Poinsett 76) from pilot test with GV3101VS225 (co-cultured in 2 ml INO).
Figure 25:
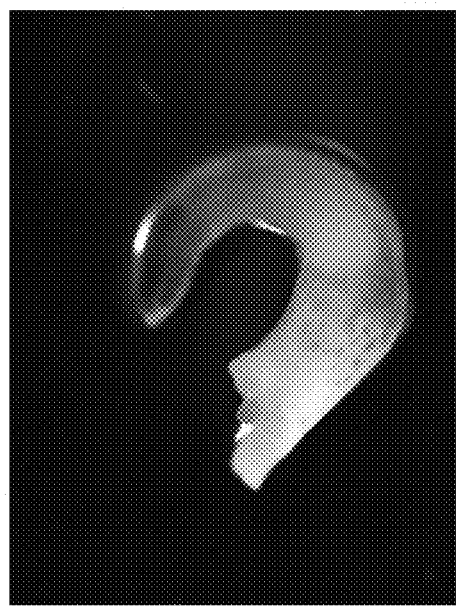
Figure 26:
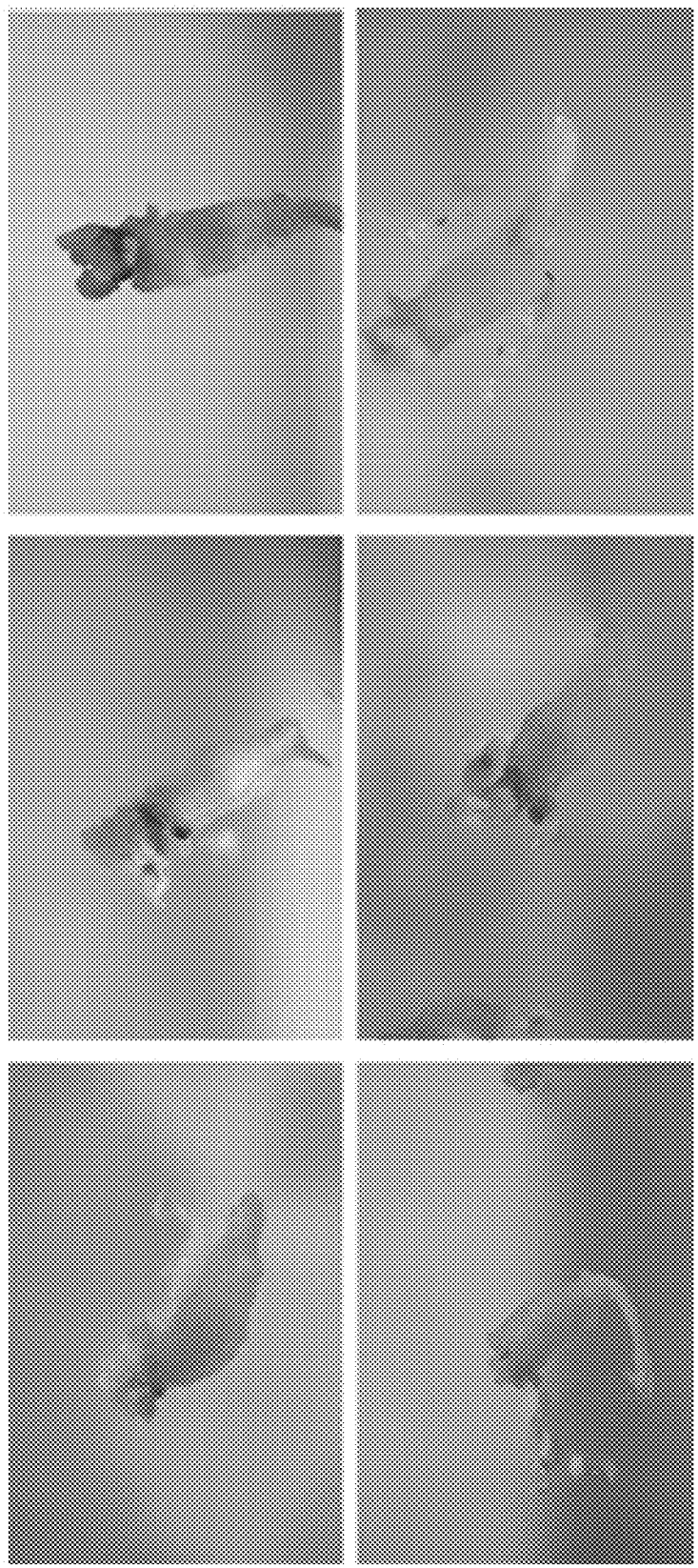
FIG. 26 shows bleached and greening sectors of cucumber explants on 200 ppm spectinomycin B5 media after about 1 month post co-culture.

We have also demonstrated transient expression in meristem explants of cucumber. Pilot transformation tests in Cucumber used the GV3101 strain. FIG. 25 shows GUS transient activity after co-culture period, which indicated we were able to transfect meristematic region in Cucumber. FIG. 26 displays bleached and greening sectors of Cucumber explants on 200 ppm spectinomycin B5 media after about 1 month post co-culture.

Example 5

Figure 20:
FIG. 20 shows regenerating cowpea explants (Crowder Mississippi Purple) at 3 weeks from mechanically isolated explants.
Figure 21:
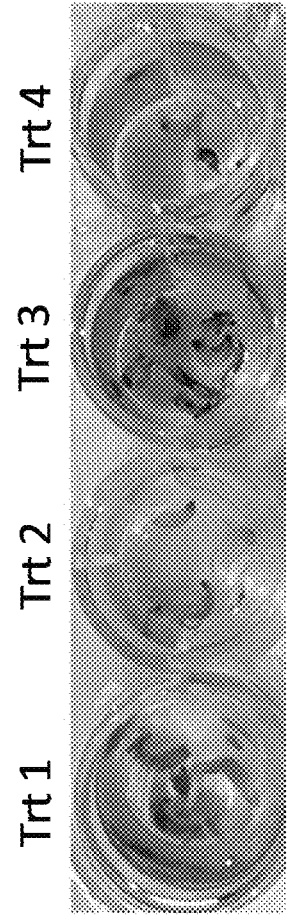
FIG. 21 shows transient GUS activity in cowpea meristem explants; machine-excised (one pass) Pinkeye Purple Hull (Trt 1); machine-excised (two passes) Pinkeye Purple Hull (Trt 2); hand-excised Crowder Mississippi Purple (Trt 3); machine-excised (one pass) Crowder Mississippi Purple (Trt 4).

We have also obtained cowpea explants from a wet machine excision process (imbibed seed) capable of regenerating on B5 media and expressing GUS transiently after inoculation with *Agrobacterium* (FIGS. 20 and 21). We believe it is possible to optimize this transformation system to accommodate mechanically isolated cowpea meristem explants as well.

Figure 22:
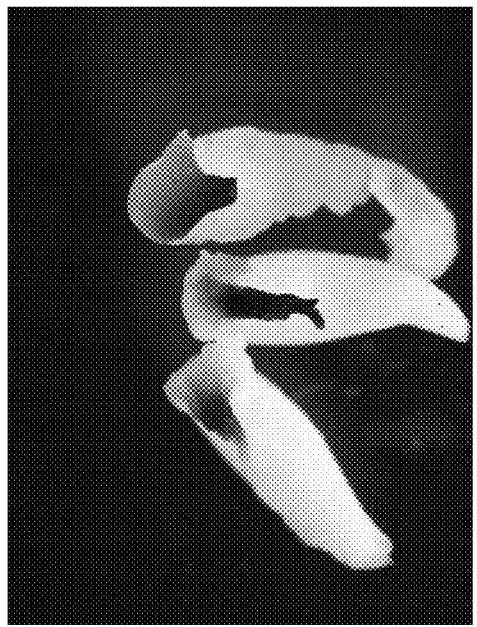
FIG. 22 shows transient GUS activity in cowpea variety IT86D-1010.
Figure 23:
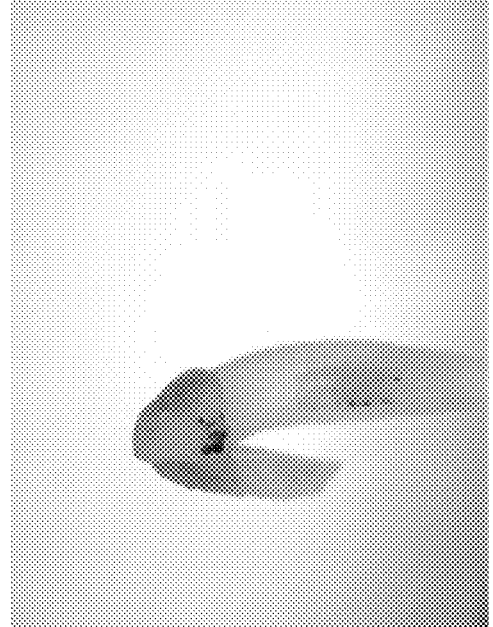
FIG. 23 show transient GUS expression in hand-excised dry bean VAE (Johnny's Yellow Eye).

Transient expression in meristematic area of hand excised (fresh) Cowpea from variety IT86D-1010 is given in FIG. 22.

We claim:
1. A method of preparing a dried explant, the method comprising the steps of
   rehydrating a dry seed in a hydration medium,
   excising meristematic tissue from the rehydrated seed, wherein the excision removes the seed coat and cotyledons, to form an explant, and
   drying the explant from at least 42 hours to fourteen days to form a dried explant.
2. The method of claim 1, wherein the hydration medium comprises one or more priming agents.
3. The method of claim 2, wherein the priming agent is selected from the group consisting of a small molecule, a nucleic acid, a polypeptide, a protein, an antibodies, a transcription factor, a biological macromolecule, a nanoparticle, and a liposome.
4. The method of claim 1, wherein the seed is a dicot.
5. The method of claim 4, wherein the seed is selected from the group consisting of cucumber, squash, pumpkin, zucchini, calabash, watermelon, alfalfa, clover, peas, beans, chickpeas, lentils, lupin bean, mesquite, carob, soybeans, peanuts, and tamarind.
6. The method of claim 1, wherein the method additionally comprises the step of incubating the explant in an incubation medium prior to drying.
7. The method of claim 1, wherein the dried explant is capable of being stored for at least 10 days.

8. The method of claim 6, wherein the explant is incubated in incubation medium comprising one or more transformation supplements.

9. The method of claim 8, wherein the transformation supplement is selected from the group consisting of a small molecule, a nucleic acid, a polypeptide, a protein, an antibodies, a transcription factor, a biological macromolecule, a nanoparticle, and a liposome.

10. The method of claim 1, wherein the method additionally comprises the step of transforming the explant or dried explant with a heterologous nucleic acid of interest.

11. The method of claim 10, wherein the explant is transformed using *Agrobacterium* mediated transformation or particle bombardment prior to drying.

12. A dried explant generated by the method of claim 1.

13. A dried explant generated by the method of claim 11.

14. A method of preparing a value-added explant, the method comprising the steps of
re-hydrating a dry seed in a hydration medium comprising at least one priming agent, and
excising meristematic tissue from the rehydrated seed, wherein the excision removes the seed coat and cotyledons, to form an explant, and
drying the explant from at least 42 hours to fourteen days in length to form a dried value-added explant.

15. The method of claim 14 wherein the priming agent is selected from the group consisting of a small molecule, a nucleic acid, a polypeptide, a protein, an antibodies, a transcription factor, a biological macromolecule, a nanoparticle, and a liposome.

16. The method of claim 14, wherein the seed is a dicot.

17. The method of claim 16 wherein the seed is selected from the group consisting of cucumber, squash, pumpkin, zucchini, calabash, watermelon, alfalfa, clover, peas, beans, chickpeas, lentils, lupin bean, mesquite, carob, soybeans, peanuts, and tamarind.

18. The method of claim 14 wherein the method additionally comprises drying the explant.

19. The method of claim 18, wherein the explant is dried in the presence of a transformation supplement.

20. The method of claim 19, wherein the transformation supplement is selected from the group consisting of a small molecule, a nucleic acid, a polypeptide, a protein, an antibodies, a transcription factor, a biological macromolecule, a nanoparticle, and a liposome.

21. The method of claim 3, wherein the priming agent is selected from the group consisting of a thidiazuron (TDZ), 6-benzylaminopurine (BAP), gibberellic acid (GA3), indole-3-acetic acid (IAA), indole-3-butyric acid (IBA), 1-naphthalaneacetic acid (NAA).

22. The method of claim 9, wherein the transformation supplement is selected from the group consisting of thidiazuron (TDZ), 6-benzylaminopurine (BAP), zeatin, kinetin, and forchlorfenuron (CPPU).

* * * * *

UNITED STATES PATENT AND TRADEMARK OFFICE
CERTIFICATE OF CORRECTION

PATENT NO. : 11,266,086 B2
APPLICATION NO. : 16/243965
DATED : March 8, 2022
INVENTOR(S) : Michael William Petersen et al.

It is certified that error appears in the above-identified patent and that said Letters Patent is hereby corrected as shown below:

In the Specification

Column 3, Line 52, "GV3101VS225" should be --GV3101/VS225--.

Column 13, Line 66, "59007-25G" should be --S9007-25G--.

Signed and Sealed this
Thirty-first Day of May, 2022

Katherine Kelly Vidal
*Director of the United States Patent and Trademark Office*